United States Patent
Motai

(10) Patent No.: US 9,795,438 B2
(45) Date of Patent: Oct. 24, 2017

(54) INCISION INSTRUMENT

(71) Applicant: OLYMPUS CORPORATION, Tokyo (JP)

(72) Inventor: Kosuke Motai, Hidaka (JP)

(73) Assignee: OLYMPUS CORPORATION, Tokyo (JP)

( * ) Notice: Subject to any disclaimer, the term of this patent is extended or adjusted under 35 U.S.C. 154(b) by 66 days.

(21) Appl. No.: 14/943,718

(22) Filed: Nov. 17, 2015

(65) Prior Publication Data
US 2016/0066976 A1  Mar. 10, 2016

Related U.S. Application Data

(63) Continuation of application No. PCT/JP2014/082546, filed on Dec. 9, 2014.

(30) Foreign Application Priority Data

Jan. 14, 2014  (JP) ................. 2014-004637

(51) Int. Cl.
*A61B 18/14* (2006.01)
*A61B 18/08* (2006.01)
(Continued)

(52) U.S. Cl.
CPC ............ *A61B 18/14* (2013.01); *A61B 18/082* (2013.01); *A61B 18/1485* (2013.01);
(Continued)

(58) Field of Classification Search
CPC ... A61B 18/082; A61B 18/1485; A61B 18/20; A61B 17/320068; A61B 18/00059;
(Continued)

(56) References Cited

U.S. PATENT DOCUMENTS

2009/0254085 A1  10/2009  Yamamoto

FOREIGN PATENT DOCUMENTS

| JP | 2006-326157 A | 12/2006 |
| JP | 2009-240380 A | 10/2009 |

(Continued)

OTHER PUBLICATIONS

Mar. 10, 2015 Search Report issued in International Patent Application No. PCT/JP2014/082546.

*Primary Examiner* — Michael Peffley
*Assistant Examiner* — Samantha Good
(74) *Attorney, Agent, or Firm* — Oliff PLC

(57) ABSTRACT

An incision instrument includes an insertion section and a manipulation section. The insertion section includes a first insulating member and an incision section inserted within the first insulating member. The incision section includes a tubular shaped first conductive member which has conductivity; a second conductive member disposed in the first conductive member; a contact section provided on an outer circumference surface of the second conductive member; and a second insulating member fixed to a distal end of the first conductive member and having an opening section. The manipulation section includes a manipulation main body section and a handle member. The second insulating member is positioned between the contact section and the first conductive section in a state in which the second conductive member is protruded from the opening section of the second insulating member.

7 Claims, 25 Drawing Sheets

(51) Int. Cl.
 A61B 18/00 (2006.01)
 A61B 17/32 (2006.01)
 A61B 18/20 (2006.01)
(52) U.S. Cl.
 CPC ....... *A61B 17/320068* (2013.01); *A61B 18/20* (2013.01); *A61B 2018/00059* (2013.01); *A61B 2018/00184* (2013.01); *A61B 2018/00196* (2013.01); *A61B 2018/00202* (2013.01); *A61B 2018/00279* (2013.01); *A61B 2018/00285* (2013.01); *A61B 2018/00559* (2013.01); *A61B 2018/00601* (2013.01); *A61B 2018/00982* (2013.01); *A61B 2018/144* (2013.01); *A61B 2018/1425* (2013.01); *A61B 2018/1475* (2013.01)
(58) Field of Classification Search
 CPC  A61B 2018/00184; A61B 2018/00196; A61B 2018/00202; A61B 2018/00279; A61B 2018/00559; A61B 2018/00601; A61B 2018/00285; A61B 2018/00982; A61B 2018/1425; A61B 2018/144; A61B 2018/1475
 See application file for complete search history.

(56) References Cited

FOREIGN PATENT DOCUMENTS

| | | |
|---|---|---|
| JP | 2010-268845 A | 12/2010 |
| WO | 2008/026689 A1 | 3/2008 |

9,795,438 B2

INCISION INSTRUMENT

This application is a continuation application based on PCT Patent Application No. PCT/JP2014/082546, filed Dec. 9, 2014, claiming priority based on Japanese Patent Application No. 2014-004637, filed Jan. 14, 2014, the contents of which are incorporated herein by reference.

FIELD OF THE INVENTION

The present invention relates to an incision instrument.

DESCRIPTION OF RELATED ART

As an example of a tool configured to dissect a biological tissue in a body, Japanese Unexamined Patent Application, First Publication No. 2006-326157 discloses a treatment tool for an endoscope that can be used in combination with an endoscope. The treatment tool for an endoscope disclosed in Japanese Unexamined Patent Application, First Publication No. 2006-326157 has an electrode through which a high frequency current is applied. The electrode of the treatment tool for an endoscope disclosed in Japanese Unexamined Patent Application, First Publication No. 2006-326157 can be used for penetration or incision of a biological tissue.

SUMMARY OF THE INVENTION

An incision instrument according to an aspect of the present invention includes an insertion section that is insertable into a body; and a manipulation section installed at a proximal end of the insertion section; wherein the insertion section includes: a first insulating member which has an elongated tubular shape, and an incision section inserted within the first insulating member; the incision section includes: a first conductive member which has a tubular shape and has conductivity, a second conductive member disposed so as to movable inside the first conductive member along a longitudinal axis of the first conductive member, an outer diameter of the second conductive member being smaller than an inner diameter of the first conductive member; a contact section provided on an outer circumference surface of the second conductive member, formed to be larger than the outer diameter of the second conductive member, and consisting of a conductor which is capable of contacting with an inner surface of the first conducive member; and a second insulating member which includes: a proximal end portion which has an outer circumference surface and an inner circumference surface, the outer circumference surface elongated inside of the distal end of the first conductive member and fixed to the distal end of the first conductive member, the inner circumference surface forming a space where the contact section is movable in an inside of the outer circumference surface; and a distal end portion in which an opening section is opened to communicate with the space and through which the second conductive member via the opening portion, the distal end portion being capable of protruding and retracting is formed at a distal end surface; and wherein the manipulation section includes: a manipulation main body section fixed to a proximal end of the first insulating member, and a handle member attached to the manipulation main body section to be movable with respect to the manipulation main body section to advance and retract the second conductive member with respect to the first conductive member and wherein the second insulating member is positioned between the contact section and the first conductive section in a state in which the second conductive member is protruded from the opening section of the second insulating member.

According to a second aspect of the present invention, in the incision instrument according to the first aspect, the second conductive member may be reciprocally movable between a storage position at which a distal end of the second conductive member is disposed in the second insulating member and an exposure position at which the second conductive member is exposed outside the second insulating member.

According to a third aspect of the present invention, in the incision instrument according to the second aspect, the manipulation section may have a connector configured to apply a high frequency current to the second conductive member; the contact section may be configured to be separated from the first conductive member in a state in which the second conductive member is positioned at the exposure position and may be configured to come in contact with the first conductive member in a state in which the second conductive member is positioned at the storage position such that the second conductive member and the first conductive member are in a conduction state; and the first conductive member may be configured to be applied a high frequency current from the second conductive member via the contact section only when the contact section is in contact with the first conductive member.

According to a fourth aspect of the present invention, in the incision instrument according to the third aspect, the manipulation section may have a stopper member configured to fix the second conductive member to the first conductive member in a state in which the contact section and the first conductive member are in contact with each other.

According to a fifth aspect of the present invention, in the incision instrument according to the first aspect, an exterior dimension of the second insulating member in a radial direction of the first conductive member may be larger than an exterior dimension of the first conductive member in the radial direction of the first conductive member.

DETAILED DESCRIPTION OF THE PREFERRED EMBODIMENTS

First Embodiment

Figure 1:
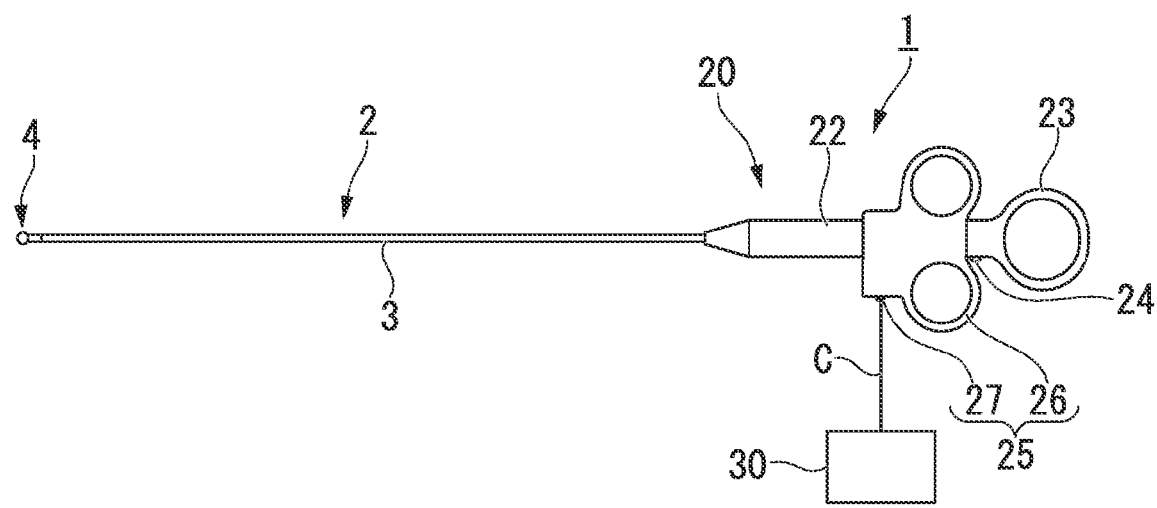
FIG. 1 is a general view showing an incision instrument according to a first embodiment of the present invention.
Figure 2:
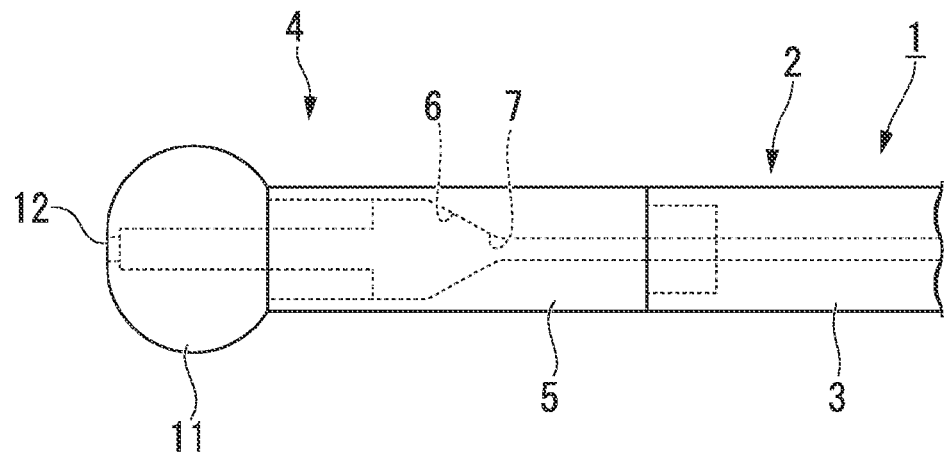
FIG. 2 is an enlarged view showing a distal portion of an insertion section of the incision instrument according to the first embodiment of the present invention.
Figure 3:
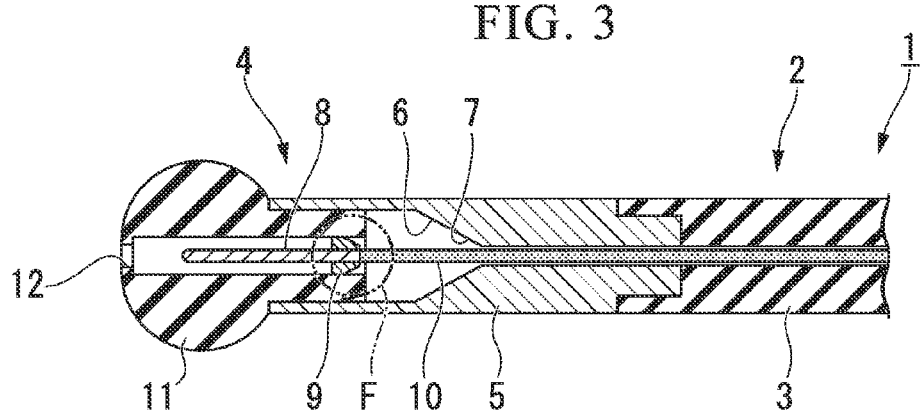
FIG. 3 is a cross-sectional view of the distal portion of the insertion section of the incision instrument according to the first embodiment of the present invention.
Figure 4:
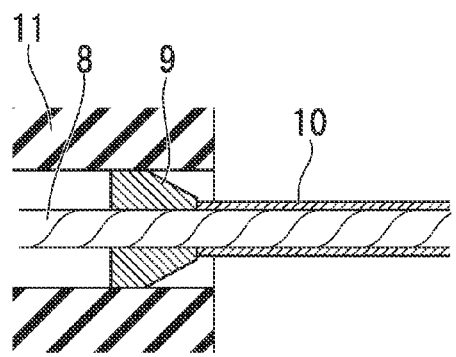
FIG. 4 is an enlarged view of a portion designated by reference character F of FIG. 3.
Figure 5:
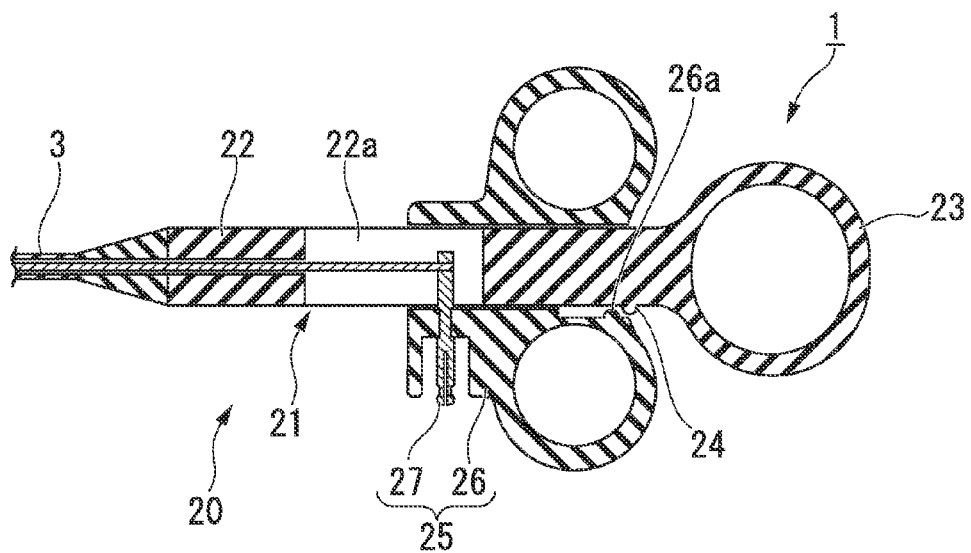
FIG. 5 is a cross-sectional view showing a manipulation section of the incision instrument according to the first embodiment of the present invention.

A first embodiment of the present invention will be described. FIG. 1 is a general view showing an incision instrument according to the first embodiment of the present invention. FIG. 2 is an enlarged view showing a distal portion of an insertion section of the incision instrument according to the first embodiment of the present invention. FIG. 3 is a cross-sectional view of the distal portion of the insertion section of the incision instrument according to the first embodiment of the present invention. FIG. 4 is an enlarged view of a portion designated by reference character F of FIG. 3. FIG. 5 is a cross-sectional view showing a manipulation section of the incision instrument according to the first embodiment of the present invention.

An incision instrument 1 according to the embodiment shown in FIG. 1 is a medical tool that can be used in incision of all of the layers of a tissue. As shown in FIG. 1, the incision instrument 1 includes an insertion section 2 which is capable of being inserted into a body, and a manipulation section 20 provided at a proximal end of the insertion section 2.

The insertion section 2 includes a first insulating member 3 and an incision section 4. The first insulating member 3 has an elongated tubular shape. The incision section 4 is inserted within the first insulating member 3.

The first insulating member 3 is a tubular insulating member. The first insulating member 3 may be rigid or may be flexible. For example, when the incision instrument 1 according to the embodiment is a tool inserted into the abdominal cavity via a trocar and used, the first insulating member 3 is preferably rigid. When the incision instrument 1 according to the embodiment is a tool inserted into a treatment tool channel of a flexible endoscope and used, the first insulating member 3 is preferably flexible.

As shown in FIGS. 2 and 3, the incision section 4 includes a first conductive member 5, a second conductive member 8 and a second insulating member 11. The first conductive member 5 is formed in a tubular shape and fixed to a distal end of the first insulating member 3. The second conductive member 8 is inserted within the first conductive member 5. The second insulating member 11 is fixed to a distal end of the first conductive member 5.

As shown in FIG. 3, the first conductive member 5 is a tube having conductivity. A proximal end of the first conductive member 5 is inserted into an opening of the distal end of the first insulating member 3. An inside of the first conductive member 5 communicates with an inside of the first insulating member 3. The first conductive member 5 is formed of, for example, a metal. The first conductive member 5 may have a configuration that an insulating material is coated with a conductor.

An outer circumferential surface of the first conductive member 5 has conductivity. A tapered section 6 is formed at a distal portion of the first conductive member 5. The tapered section 6 is formed to have an inner surface of the first conductive member 5 inclined in a conical shape such that an inner diameter at a distal side is large and an inner diameter at a proximal side is small. A contact surface 7 is formed at at least a proximal portion of the tapered section 6 in the inner surface of the first conductive member 5. The contact surface 7 has conductivity. The contact surface 7 is configured to be electrically connected to the outer circumferential surface of the first conductive member 5.

The second conductive member 8 is disposed in the first conductive member 5 configured to protrude from and retract to the opening of the distal end of the first conductive member 5. The second conductive member 8 has a contact section 9 that can come in contact with the contact surface 7 formed at the inner surface of the first conductive member 5. In the embodiment, the outer surface of the second conductive member 8 is coated with a material having an insulation property at a region where is closer to a proximal side than the contact section 9. Specifically, an insulating film 10 is formed on the outer surface of the second conductive member 8 at a region where is closer to the proximal side than the contact section 9.

As shown in FIG. 4, the contact section 9 is formed of a conductor and fixed to an outer circumferential surface of the second conductive member 8. The contact section 9 of the embodiment has a larger diameter than the second conductive member 8. In addition, the contact section 9 has a diameter larger than the inner diameter of the proximal end of the tapered section 6 of the first conductive member 5. For this reason, the contact section 9 can come in contact with the inner circumferential surface of the tapered section 6 at the proximal portion of the tapered section 6. That is, the contact section 9 can contact with the contact surface 7 formed at the tapered section 6. When the contact section 9 contacts with the contact surface 7, the second conductive member 8 and the first conductive member 5 are in a conduction state.

A position of the contact section 9 in the second conductive member 8 is set based on a relation between a position of the distal end of the second conductive member 8 and a position of an opening section 12 of the second insulating member 11 (to be described below). That is, the contact section 9 is disposed at a position on the second conductive member 8 such that the contact section 9 comes in contact with the contact surface 7 when the distal end of the second conductive member 8 is positioned closer to the proximal side than the opening section 12 and the contact section 9 is separated from the contact surface 7 when the distal end of the second conductive member 8 is positioned closer to the distal side than the opening section 12. In the embodiment, the contact section 9 is positioned apart from the first conductive member 5 such that the second insulating member 11 is positioned therebetween when the distal end of the second conductive member 8 is exposed from the opening section 12 to be used for penetration treatment.

The second insulating member 11 is an insulating member fixed to the distal end of the first conductive member 5 and the inner circumferential surface of the first conductive member 5 so as to cover the distal end of the first conductive member 5. The second insulating member 11 has the opening section 12 through which the second conductive member 8 is capable of protruding and retracting.

The opening section 12 has a penetration hole having a size into which the second conductive member 8 can be inserted and the contact section 9 cannot be inserted. Accordingly, a maximum length of the second conductive member 8 protruding from the opening section 12 is restricted to a predetermined length by contacting the contact section 9 with the opening section 12. A protrusion length of the second conductive member 8 from the opening section 12 when the contact section 9 contacts with the opening section 12 is set according to a thickness of a target tissue of all layer incision. That is, a protrusion length of the second conductive member 8 from the opening section 12 when the contact section 9 contacts with the opening section 12 is set to a length with which the distal end of the second conductive member 8 exits a surface opposite to a surface of a puncture side of the target tissue of all layer incision when a distal end surface of the opening section 12 comes in contact with the surface of the puncture side of the target tissue. If the protrusion length of the second conductive member 8 is excessively long, when the second conductive member 8 penetrates the tissue, a contact of the distal end of the second conductive member 8 with the other tissue except for the target tissue of the penetration may occur. For this reason, the protrusion length of the second conductive member 8 from the opening section 12 when the contact section 9 contacts with the opening section 12 is set in consideration of a necessary and sufficient penetration length of the second conductive member 8 through the penetration target tissue.

An exterior dimension of the second insulating member 11 in the radial direction of the first conductive member 5 is larger than an exterior dimension of the first conductive member 5 in the radial direction of the first conductive member 5.

A surface of the second insulating member 11 directed toward the distal side is inclined such that the outer diameter is gradually increased toward the proximal side. A surface of the second insulating member 11 directed toward the distal side expands the biological tissue when the second insulating member 11 is inserted into the biological tissue.

A surface of the second insulating member 11 directed toward the proximal side is inclined such that the outer diameter is gradually increased toward the distal side. A surface of the second insulating member 11 directed toward the proximal side guides the biological tissue to the first conductive member 5 when all of the layers of the biological tissue are incised using the incision section 4.

In the embodiment, the second insulating member 11 has an exterior shape formed in a spherical shape as a whole.

As shown in FIG. 5, the manipulation section 20 includes a manipulation main body section 21 and a handle member 25.

The manipulation main body section 21 includes a shaft body 22, a ring section 23 and a stopper member 24. The shaft body 22 is fixed to the proximal end of the first insulating member 3. The ring section 23 is disposed at the proximal end of the shaft body 22. The stopper member 24 is engaged with the handle member 25.

The shaft body 22 is a substantially tubular insulating member into which the second conductive member 8 is inserted. The shaft body 22 has a groove 22a into which a connector 27 (to be described below) provided at the handle member 25 is inserted.

The ring section 23 has a penetration hole having an outer diameter larger than the exterior shape of the shaft body 22 and into which an operator's finger is inserted.

The stopper member 24 has a shape in which the outer surface of the shaft body 22 is raised such that the handle member 25 encounters resistance when the handle member 25 moves toward the proximal side beyond the stopper member 24. A position of the stopper member 24 is set to correspond to a positional relation between the contact section 9 and the contact surface 7. That is, a position of the stopper member 24 is set such that a protrusion 26a of a slider section 26 of the handle member 25 is disposed in the vicinity of the proximal side of the stopper member 24 when the contact section 9 and the contact surface 7 come in contact with each other.

The handle member 25 is attached to the manipulation main body section 21 to advance and retract the second conductive member 8 with respect to the first conductive member 5. In the embodiment, the handle member 25 includes the slider section 26 and the connector 27. The slider section 26 is connected to the shaft body 22 to advance and retract with respect to the shaft body 22 along a centerline of the shaft body 22. The connector 27 is fixed to the slider section 26 and fixed to a proximal end of the second conductive member 8.

The slider section 26 is provided with at least one penetration hole such that the operator's finger is insertable. In the embodiment, the slider section 26 is provided with two penetration holes. The slider section 26 is able to advance and retract with respect to the shaft body 22 in a centerline direction of the shaft body 22. The protrusion 26a engaged with the stopper member 24 is formed at the slider section 26. The protrusion 26a formed at the slider section 26 is capable of coming in contact with the stopper member 24 such that the slider section 26 is receive resistance when the protrusion 26a climbs over the stopper member 24. When the slider section 26 advances and retracts with respect to the shaft body 22, the second conductive member 8 reciprocates with respect to the first conductive member 5 between a storage position and an exposure position. The storage position is a position at which the distal end of the second conductive member 8 is disposed in the second insulating member 11. The exposure position is a position at which the second conductive member 8 is exposed outside the second insulating member 11.

The connector 27 is a conductive member being configured to be capable of attaching a cord C for connecting a high frequency power supply apparatus 30. The connector 27 is installed to apply a high frequency current to the second conductive member 8.

An action of the incision instrument 1 according to the embodiment will be described. FIGS. 6 to 13 are views used to explain the action of the incision instrument of the embodiment. Specifically, a total laparoscopic hysterectomy (TLH) using the incision instrument 1 according to the embodiment is shown as an example.

In the total laparoscopic hysterectomy, the womb is separated by treatment of incising the vaginal canal after treatment for a plurality of ligaments, blood vessels, adhered tissues and adnexa configured to support the womb.

In the embodiment, the womb is dissected from the vaginal canal using a boundary portion between the womb neck area and the vaginal canal as a dissection line. First, the treatments for the plurality of ligaments supporting the womb, blood vessels, adhered tissues and adnexa are performed by known procedures. The procedures are performed under a laparoscopic observation. In addition, according to necessity, the womb manipulator may be inserted into the womb from the vaginal canal to adjust the position of the womb.

Figure 6:
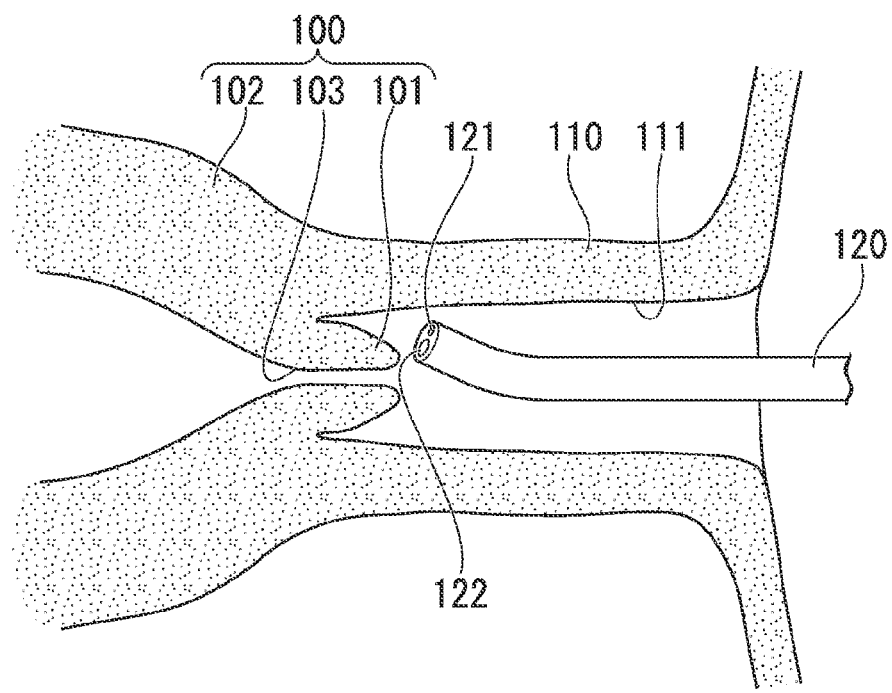
FIG. 6 is a view used to explain an action of the incision instrument according to the first embodiment of the present invention.

Next, as shown in FIG. 6, a flexible endoscope 120 is inserted into the vaginal canal 110. The flexible endoscope 120 used in the embodiment includes an observation device 121 and a treatment tool channel 122. The observation device 121 is used to observe an incision area. The incision instrument 1 according to the embodiment is inserted into the treatment tool channel 122.

Figure 7:
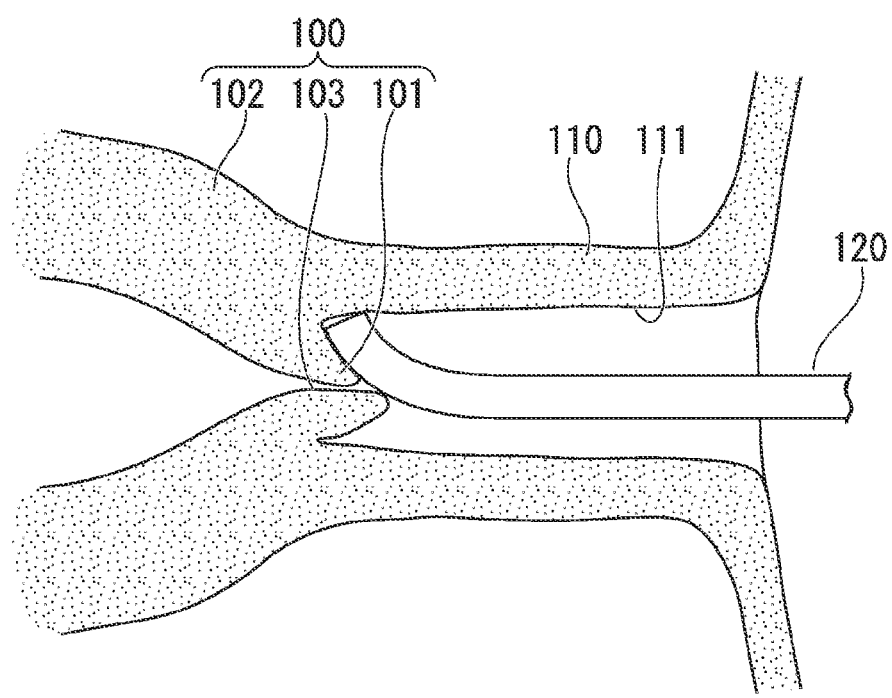
FIG. 7 is a view used to explain the action of the incision instrument according to the first embodiment of the present invention.

Next, as shown in FIG. 7, the observation device 121 of the flexible endoscope 120 and a distal end of the treatment tool channel 122 are guided to the vicinity of an incision-scheduled area. Further, the insertion section 2 of the incision instrument 1 is inserted from a proximal end side of the treatment tool channel 122 of the flexible endoscope 120.

In a process of guiding the distal end of the incision instrument 1 to the incision-scheduled area, the protrusion 26a of the slider section 26 is disposed at the distal side of the stopper member 24 and in the vicinity of the stopper member 24. In the process of guiding the distal end of the incision instrument 1 to the incision-scheduled area, the distal end of the second conductive member 8 is disposed at the proximal side of the opening of the second insulating member 11, and the contact section 9 is separated from the contact surface 7. For this reason, the second conductive member 8 is housed in the second insulating member 11, and the high frequency current cannot be applied to the first conductive member 5. Accordingly, in the process of guiding the distal end of the incision instrument 1 to the incision-scheduled area, even when the high frequency current is applied to the connector 27 from the high frequency power supply apparatus 30, the high frequency current is not applied to the biological tissue. For this reason, even when the outer surface of the first conductive member 5 comes in contact with the biological tissue, the biological tissue is not incised.

Figure 8:
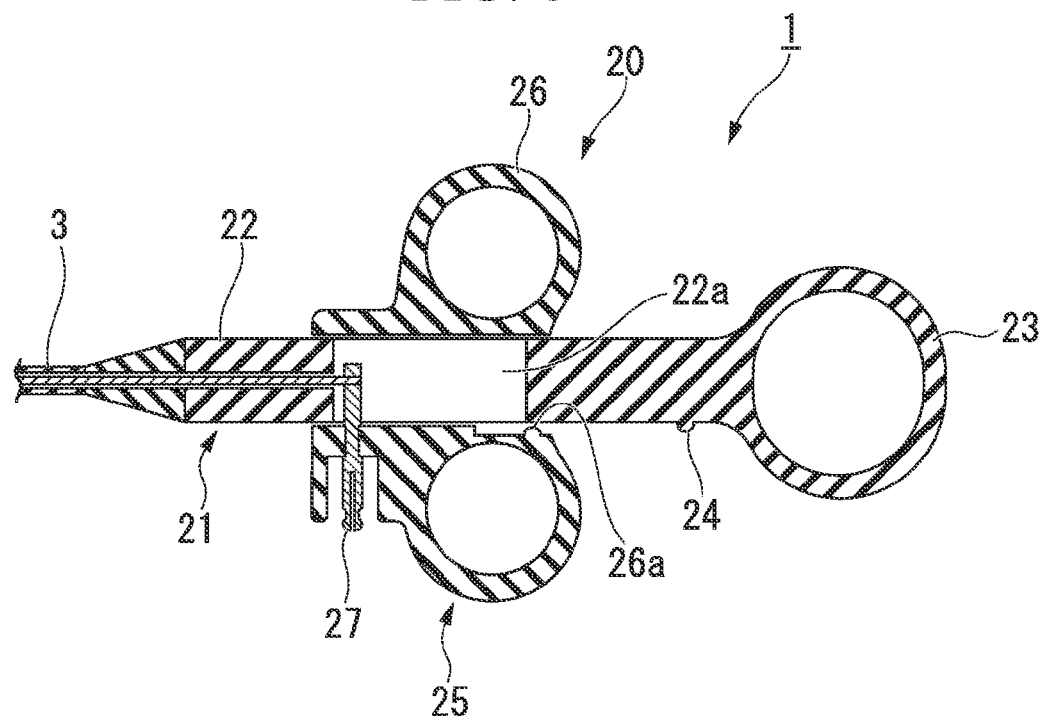
FIG. 8 is a cross-sectional view showing the manipulation section of the incision instrument according to the first embodiment of the present invention.
Figure 9:
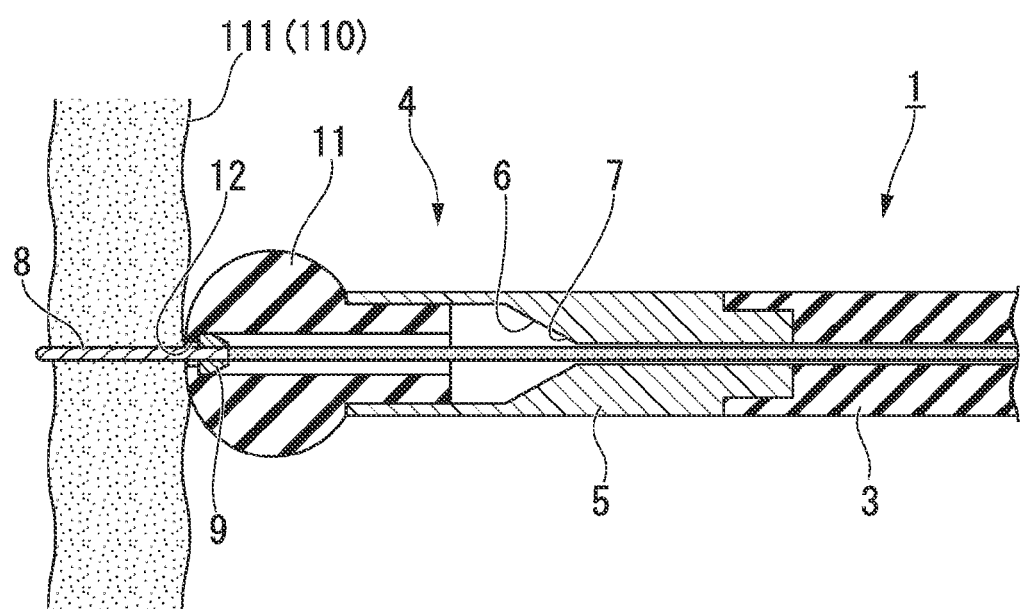
FIG. 9 is a view used to explain the action of the incision instrument according to the first embodiment of the present invention.

The operator inserts the distal end of the insertion section 2 of the incision instrument 1 to a predetermined dissection line of the vaginal canal 110 that is to be incised. Next, as shown in FIG. 8, the operator moves the handle member 25 of the incision instrument 1 to the distal side. Accordingly, the distal end of the second conductive member 8 protrudes from the opening of the second insulating member 11. After that, when the high frequency current is applied to the connector 27 from the high frequency power supply apparatus 30, the high frequency current is applied to the second conductive member 8 from the connector 27. In a state in which the high frequency current is applied to the second conductive member 8, as shown in FIG. 9, the operator pierces the distal end of the second conductive member 8 at the dissection line. Accordingly, the second conductive member 8 penetrates a vaginal wall 111 at the dissection line. The operator of the incision instrument 1 inserts the second conductive member 8 until the second insulating member 11 comes in contact with the penetration target tissue (the vaginal wall 111). Accordingly, the distal end of the second conductive member 8 penetrates the penetration target tissue in the thickness direction and is exposed to an opposite side.

Figure 10:
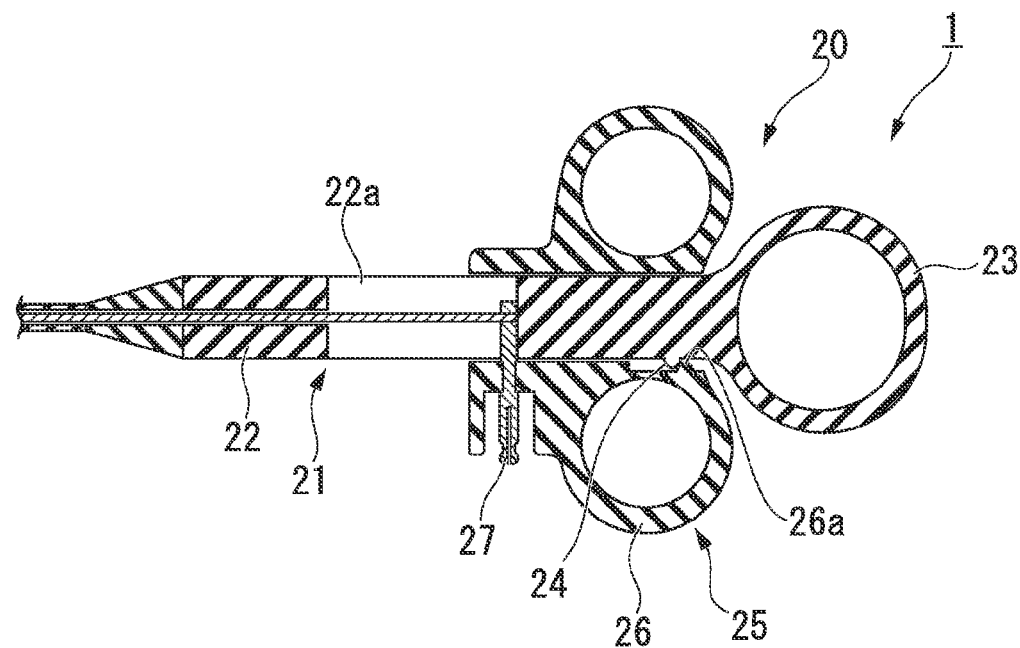
FIG. 10 is a cross-sectional view showing the manipulation section of the incision instrument according to the first embodiment of the present invention.
Figure 11:
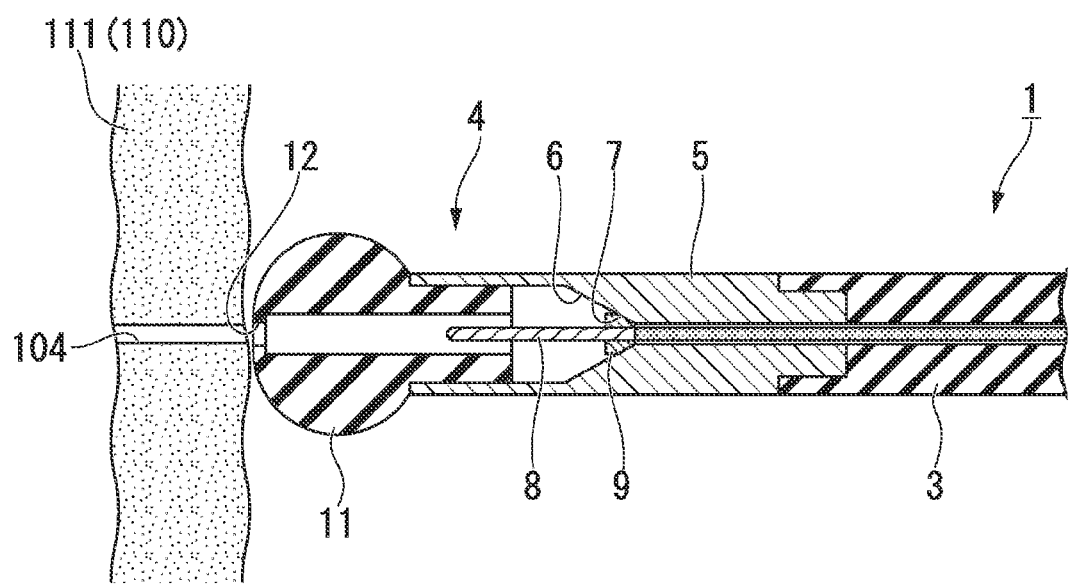
FIG. 11 is a view used to explain the action of the incision instrument according to the first embodiment of the present invention.

As the second conductive member 8 penetrates the vaginal canal 110, a penetration hole 104, which communicates the abdominal cavity with the inside of the vagina, is formed in the vaginal canal 110 on the dissection line. The operator moves the handle member 25 to the proximal side of the shaft body 22 so as to cause the handle member 25 to climb over the stopper member 24, and as shown in FIG. 10, disposes the handle member 25 at the proximal side of the stopper member 24. Thereby, as shown in FIG. 11, the distal end of the second conductive member 8 is stored in the opening of the second insulating member 11, and further, the contact section 9 comes in contact with the contact surface 7 to electrically connect the first conductive member 5 to the second conductive member 8 via the contact section 9.

When the protrusion 26a of the slider section 26 of the handle member 25 is disposed in the vicinity of the proximal side of the stopper member 24, the handle member 25 is restricted a movement toward the distal side of the stopper member 24. For this reason, in the distal portion of the insertion section 2, the second conductive member 8 is fixed with respect to the first conductive member 5 in a state in which the contact section 9 and the contact surface 7 are in contact with each other. In a state in which the protrusion 26a is disposed in the vicinity of the proximal side of the stopper member 24, the handle member 25 pulls the second conductive member 8 toward the proximal side such that the contact section 9 is further pulled toward the proximal side in a state in which the contact section 9 is in contact with the contact surface 7. For this reason, the contact section 9 is pressed against the contact surface 7. In the embodiment, since the contact surface 7 is formed at the tapered section 6, the contact section 9 is pulled in a direction in which the contact section 9 is further moved toward the proximal side by a force with which the handle member 25 pulls the second conductive member 8 in a state in which the contact section 9 is in contact with the contact surface 7, the contact section 9 is strongly connected to the contact surface 7 so as to bite into the contact surface 7, and the connection state is maintained by the stopper member 24.

Figure 12:
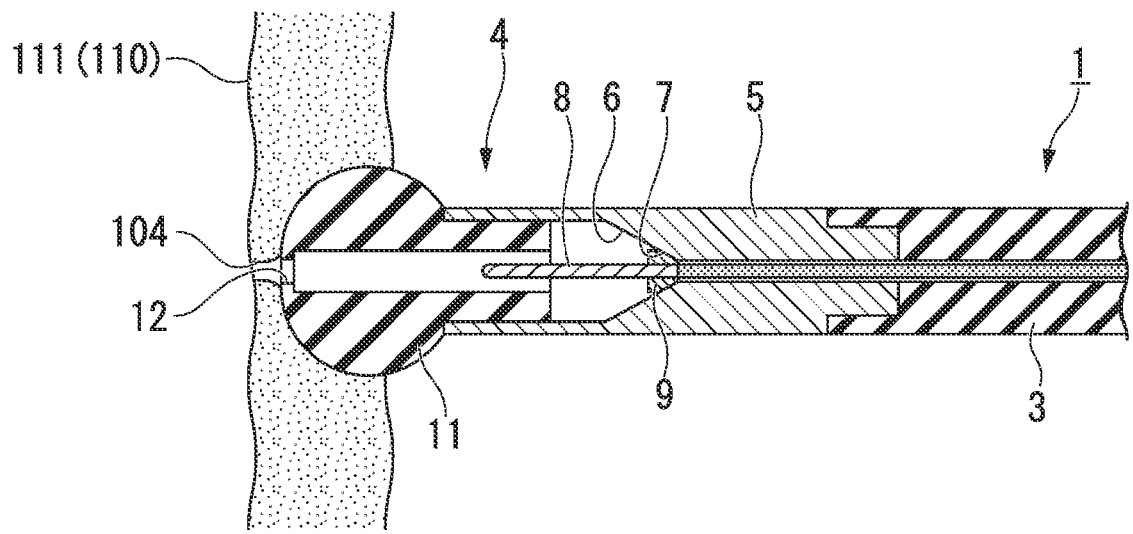
FIG. 12 is a view used to explain the action of the incision instrument according to the first embodiment of the present invention.
Figure 13:
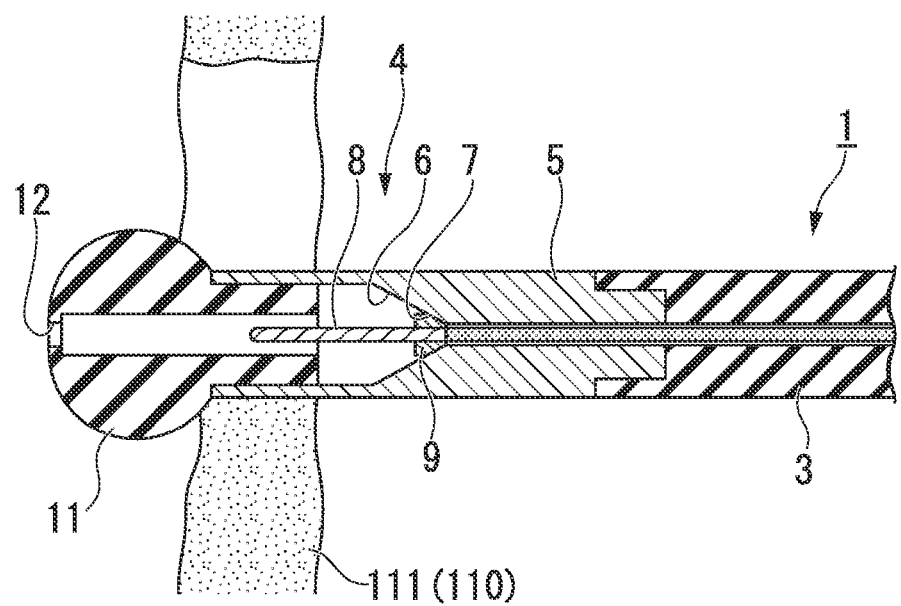
FIG. 13 is a view used to explain the action of the incision instrument according to the first embodiment of the present invention.

As shown in FIG. 12, the operator pierces the distal side of the second insulating member 11 into the penetration hole 104 formed in the vaginal canal 110 using the second conductive member 8. The surface directed toward the distal side of the second insulating member 11 expands the penetration area and the second insulating member 11 moves toward the opposite side. As shown in FIG. 13, in a state in which the second insulating member 11 penetrates the vaginal canal 110, the outer circumferential surface of the first conductive member 5 can come in contact with the vaginal canal 110. The operator applies the high frequency current to the connector 27 in a state in which the first conductive member 5 is in contact with the vaginal canal 110. As a result, the high frequency current applied to the second conductive member 8 from the connector 27 is applied to the first conductive member 5 through the contact section 9, and the vaginal canal 110 is incised by the first conductive member 5. As shown in FIG. 13, the operator incises the vaginal canal 110 along the dissection line by moving the first conductive member 5 along the dissection line. According to necessity, the above-mentioned procedures of penetration and incision are performed also in another place on the dissection line, and the womb 100 is dissected from the vaginal canal 110.

As described above, in the incision instrument 1 according to the embodiment, after penetrating the biological tissue using the second conductive member 8, the second conductive member 8 is housed in the second insulating member 11, and then, the first conductive member 5 comes in contact with the penetration hole 104 formed by the second conductive member 8, thereby the all layer of the biological tissue can be incised. For this reason, in the process of the all layer incision of the biological tissue, even when the distal end of the first conductive member 5 comes in contact with the area in which the incision is not scheduled, the area is not incised. As a result, the all layer incision of the biological tissue is safely and easily performed.

According to the incision instrument 1 of the embodiment, in comparison with the case in which the tool for penetration and a separate tool for all layer incisions are sequentially used, the procedure can be rapidly preceded.

The high frequency current is applied to the first conductive member 5 from the second conductive member 8 via the contact section 9 only when the contact section 9 is in contact with the contact surface 7 of the first conductive member 5. That is, incision of the biological tissue using the first conductive member 5 can be performed only in a state in which the contact section 9 is in contact with the contact surface 7. As a result, the procedure in which the second conductive member 8 penetrates the biological tissue can be performed when the second conductive member 8 is at the exposure position, and the procedure in which the all of the layers of the biological tissue are incised by the first conductive member 5 can be performed when the second conductive member 8 is at the storage position.

In a state in which movement of the stopper member 24 toward the distal side of the handle member 25 is restricted, the contact section 9 is pushed against the contact surface 7 at the distal portion of the insertion section 2. For this reason, the high frequency current can be securely applied to the first conductive member 5 in the process of the all layer incision using the first conductive member 5.

The exterior dimension of the second insulating member 11 in the radial direction of the first conductive member 5 is larger than the exterior dimension of the first conductive member 5 in the radial direction of the first conductive member 5. For this reason, after the second insulating member 11 is inserted into the penetration hole 104 formed using the second conductive member 8, the second insulating member 11 hardly comes off the penetration hole 104. For this reason, since the first conductive member 5 is hardly removed from the biological tissue during the all layer incision of the biological tissue, the dissection along the dissection line becomes easy.

Second Embodiment

Next, a second embodiment of the present invention will be described.

Figure 14:
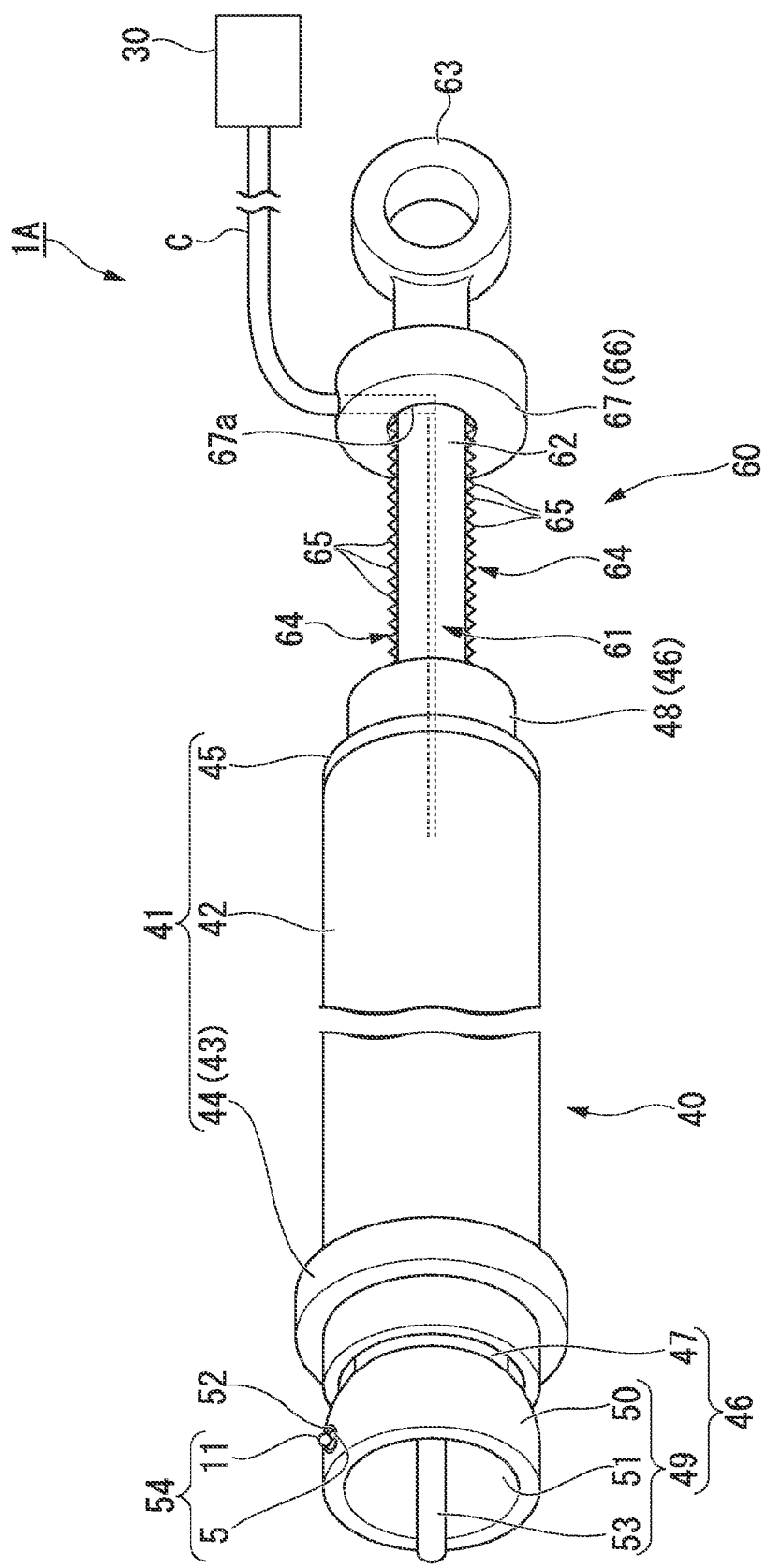
FIG. 14 is a general view showing an incision instrument according to a second embodiment of the present invention.
Figure 15:
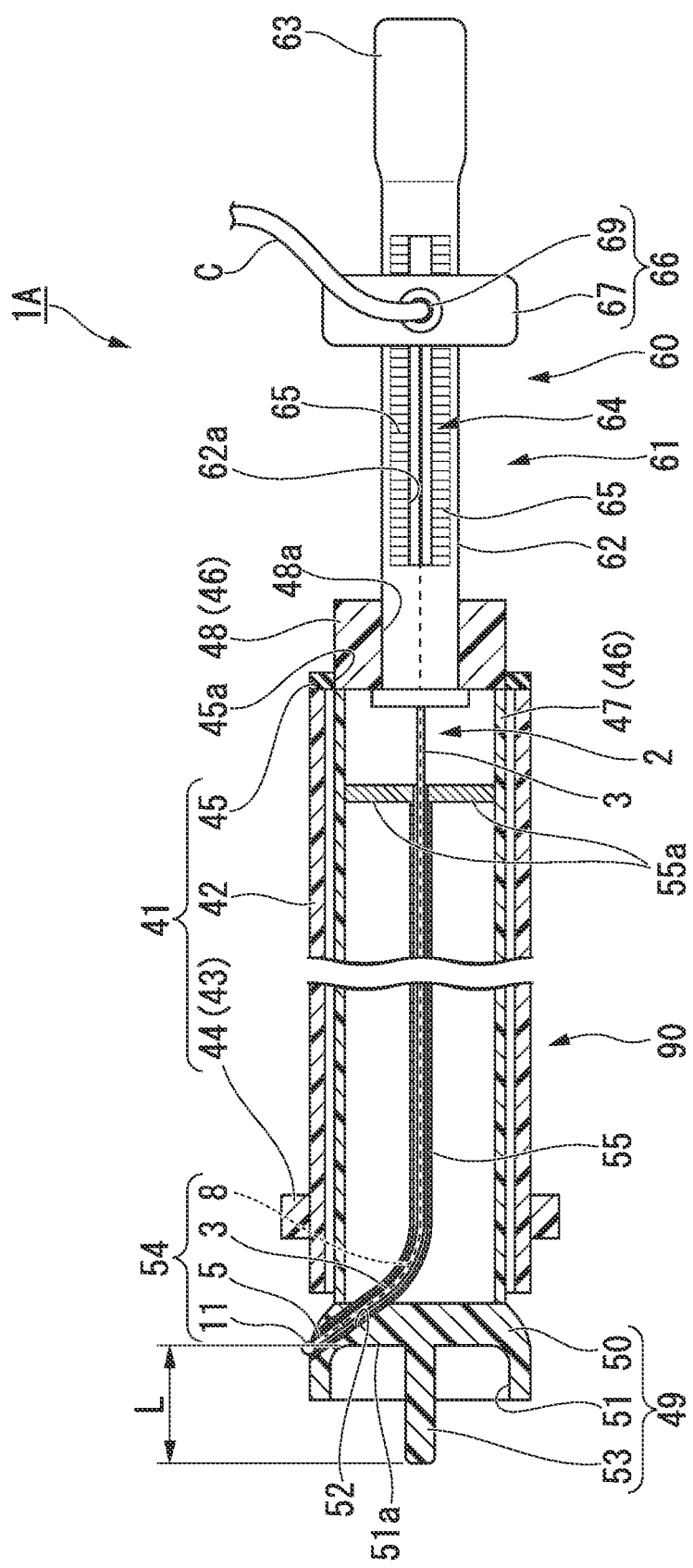
FIG. 15 is a partial cross-sectional view of the incision instrument according to the second embodiment of the present invention.
Figure 16:
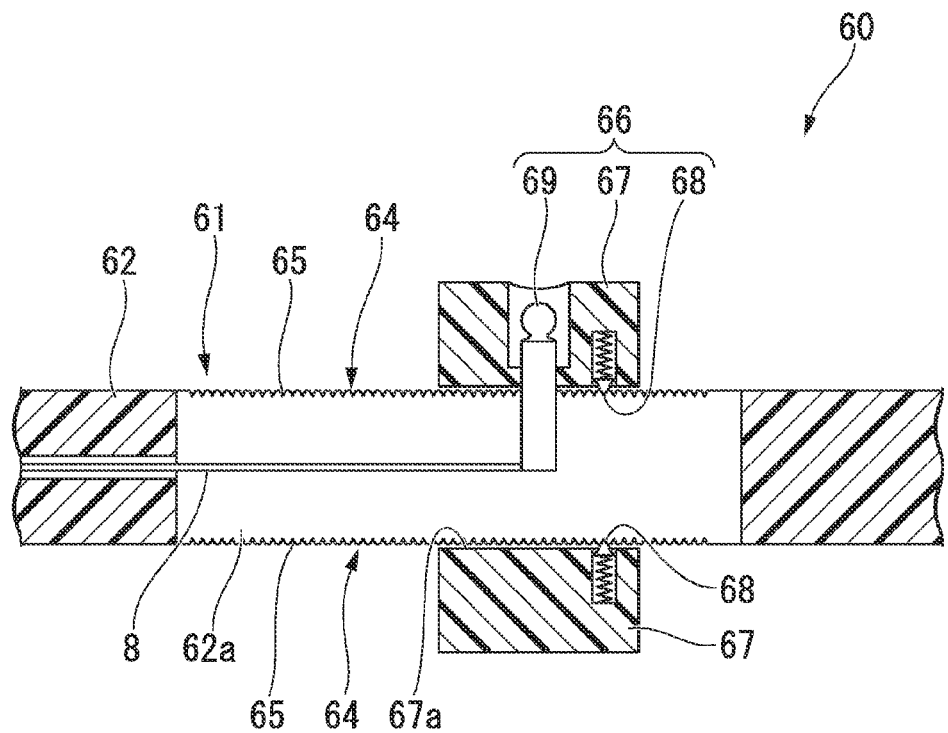
FIG. 16 is a partial cross-sectional view of a manipulation section of the incision instrument according to the second embodiment of the present invention.

An incision instrument 1A according to the embodiment is a medical tool having an insertion section 2 described in the first embodiment and is suitable to perform all layer incision of the vaginal wall 111. FIG. 14 is a general view showing the incision instrument 1A according to the embodiment. FIG. 15 is a partial cross-sectional view of the incision instrument 1A according to the embodiment. FIG. 16 is a cross-sectional view of a manipulation section 60 of the incision instrument 1A according to the embodiment.

The whole of the incision instrument 1A has a substantially rod shape. The incision instrument 1A includes a main body section 40, an incision section 54 and the manipulation section 60.

As shown in FIGS. 14 and 15, the whole of the main body section 40 has a substantially rod shape. The distal side of the main body section 40 is configured to be inserted into the vaginal canal. The main body section 40 includes an exterior section 41 and an interior section 46.

The exterior section 41 configures the outermost layer in the main body section 40. The exterior section 41 includes an outer tube member 42, a locking section 43 and an airtight valve 45.

The outer tube member 42 has a tubular shape having an exterior dimension which is insertable into the vaginal canal. The outer tube member 42 has rigidity or slight elasticity. In the embodiment, the outer tube member 42 is formed of a resin or the like. For example, a fluorine-based resin (for example, polytetrafluoroethylene), a nylon-based resin (for example, Nylon) or an olefin-based resin (for example, polyethylene or polypropylene) is provided as a material of the outer tube member 42. The outer circumferential surface of the outer tube member 42 has a smoothly curved surface that does not damage a mucous membrane.

The locking section 43 has an annular member 44 fixed to the outer circumferential surface of the outer tube member 42. The annular member 44 is disposed in the vicinity of the distal end of the outer tube member 42. The annular member 44 extends in the circumferential direction of the outer tube member 42 on the outer circumferential surface of the outer tube member 42. The annular member 44 and the outer tube member 42 are fixed by, for example, adhesion. The annular member 44 and the outer tube member 42 may be integrally formed with each other.

The annular member 44 protrudes outward from the outer circumferential surface of the outer tube member 42 in the radial direction of the outer tube member 42. The outer circumferential surface of the annular member 44 has a smoothly curved surface that does not damage a mucous membrane. The annular member 44 serves to airtightly close the gap between the outer tube member 42 and the vaginal wall 111 upon use of the incision instrument 1A. The annular member 44 serves such that the vaginal wall 111 is prevented from moving with respect to the outer tube member 42 upon incision of the vaginal wall 111.

The airtight valve 45 is a valve configured to airtightly close the outer tube member 42 and the interior section 46. The airtight valve 45 is fixed to the opening of the proximal end of the outer tube member 42. The airtight valve 45 has an annular shape having a hole 45a. The interior section 46 can be inserted into the hole 45a formed in the airtight valve 45. The airtight valve 45 is airtightly and slidably adhered to a connecting member 48 in a state in which the connecting member 48 (to be described below) of the interior section 46 is inserted into the hole 45a. The airtight valve 45 has elasticity. A centerline of the opening of the hole 45a of the airtight valve 45 coincides with a centerline of the outer tube member 42. The airtight valve 45 supports the connecting member 48 such that the connecting member 48 is rotatable about the centerline of the outer tube member 42 serving as a rotational center. A material of the airtight valve 45 is not particularly limited as long as the material has elasticity. In the embodiment, the airtight valve 45 is formed of a material such as silicon or urethane.

The interior section 46 is rotatable in the outer tube member 42 about the centerline of the outer tube member 42 serving as a rotational center. As shown in FIG. 15, the interior section 46 includes an inner tube member 47, the connecting member 48 and an abutting section 49.

The inner tube member 47 is a tubular member disposed in the outer tube member 42. An outer diameter dimension of the inner tube member 47 is slightly smaller than an inner diameter dimension of the outer tube member 42. A centerline of the inner tube member 47 is substantially concentric with a centerline of the outer tube member 42. The inner tube member 47 has hardness such that a force of rotating the manipulation section 60 about the centerline of the outer tube member 42 serving as a rotational center can be transmitted to the abutting section 49.

The connecting member 48 connects a distal end of a shaft body 62 of a shaft section 61 of the manipulation section 60 (to be described below) and a proximal end of the inner tube member 47. The connecting member 48 has a substantially cylindrical shape having a hole 48a. The outer circumferential surface of the connecting member 48 is in close contact with an inner surface of the hole 45a of the airtight valve 45. A distal end of the shaft body 62 of the manipulation section 60 is inserted into the hole 48a formed in the connecting member 48. The connecting member 48 supports the shaft body 62 such that the shaft body 62 inserted into the hole 48a can advance and retract in the hole 48a. The connecting member 48 is engaged with the shaft body 62 so as to rotate with the shaft body 62 when the shaft body 62 is rotated about the centerline of the shaft body 62 serving as a rotational center.

The abutting section 49 is disposed at the distal portion of the interior section 46. The abutting section 49 is configured to be capable of contacting with a portion 101 (see FIG. 7, hereinafter, referred to as "a first portion 101") of the uterine cervix 102 exposed in the vaginal canal 110 upon use of the incision instrument 1A. The abutting section 49 of the embodiment includes a cup-shaped member 50 and a positioning member 53. The cup-shaped member 50 has a cup shape having a diameter that is gradually increased toward the distal side. The positioning member 53 protrudes from an inner surface of the cup-shaped member 50.

The cup-shaped member 50 is fixed to a distal end of the inner tube member 47. The cup-shaped member 50 has a concave surface section 51 and a guide hole 52. The concave surface section 51 is configured to be capable of contacting with the first portion 101. The guide hole 52 communicates with an inside of the inner tube member 47 and is formed elongated in a direction inclined with respect to the centerline of the inner tube member 47.

A distal end of a tubular sheath 55 (to be described below) is fixed to the guide hole 52 of the cup-shaped member 50. The guide hole 52 restricts the movement directions of the insertion section 2 and the second conductive member 8 which are capable of protruding from the sheath 55 of the incision section 54 to a predetermined direction inclined with respect to the centerline of the inner tube member 47. The guide hole 52 guides the advancing and retreating of the insertion section 2 and the second conductive member 8 such that the distal end of the insertion section 2 and the distal end of the second conductive member 8 move to be inclined outward in the radial direction of the inner tube member 47 when the insertion section 2 and the second conductive member 8 are moved toward the distal side of the inner tube member 47. An inclination angle of the centerline of the guide hole 52 with respect to the centerline of the inner tube member 47 is set to an angle at which the distal ends of the first conductive member 5 and the second conductive member 8 are separated from the uterine cervix or the uterine body without contact with the uterine cervix or the uterine body upon use of the incision instrument 1A.

The positioning member 53 is a rod-shaped member protruding from a bottom section of the concave surface section 51 of the cup-shaped member 50 toward the distal side thereof. The positioning member 53 extends on the same axis as the centerline of the inner tube member 47. As shown in FIG. 15, a protrusion length L of the positioning member 53 from a bottom surface 51a of the concave surface section 51 is set such that at least the distal end of the positioning member 53 is inserted into the orifice of the uterus 103 in a state in which the concave surface section 51 of the cup-shaped member 50 is in contact with the first portion 101 as shown in FIG. 17.

Figure 17:
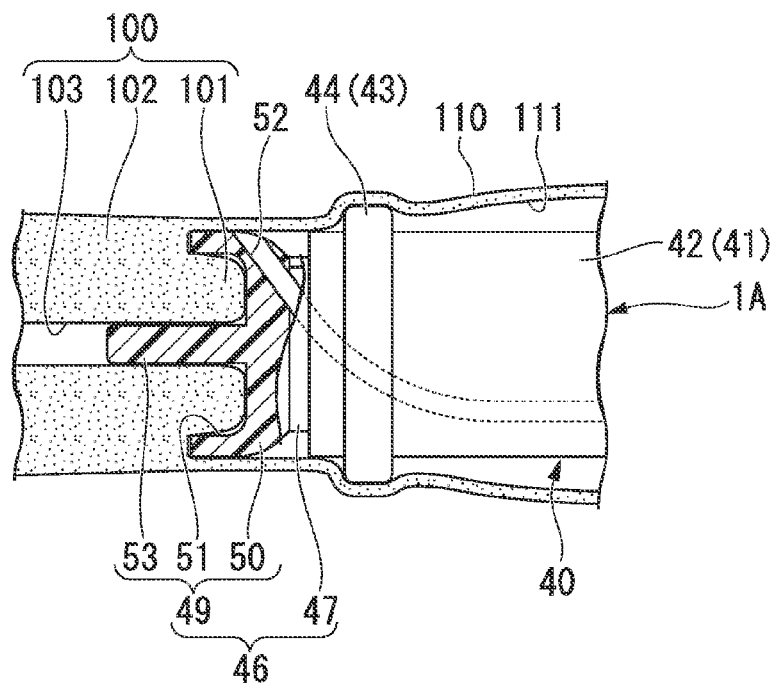
FIG. 17 is a view used to explain an action of the incision instrument according to the second embodiment of the present invention.

As shown in FIG. 17, the positioning member 53 is configured to be capable of connecting the orifice of the uterus 103 and the abutting section 49 such that the abutting section 49 is rotatable about the orifice of the uterus 103 serving as a rotational center. In a state in which the positioning member 53 is inserted into the orifice of the uterus 103 and the abutting section 49 connects the orifice of the uterus 103, the insertion section 2 disposed at the guide hole 52 of the cup-shaped member 50 is rotatable about the orifice of the uterus 103 serving as a rotational center.

The incision section 54 includes the insertion section 2 described in the first embodiment, the sheath 55 and the manipulation section 60. The insertion section 2 is inserted through the sheath 55 so as to advance and retract. The manipulation section 60 is fixed to the connecting member 48.

The distal end of the insertion section 2 is supported by the guide hole 52 formed in the cup-shaped member 50 via the sheath 55. The proximal end of the insertion section 2 is fixed to a slider 66 of the manipulation section 60 (to be described below). The proximal end of the second conductive member 8 is fixed to a connector 69 (to be described below) installed at the slider 66. The second conductive member 8 and a connector 69 are electrically connected to each other. An intermediate section of the second conductive member 8 is disposed in the inner tube member 47.

The sheath 55 has a cylindrical shape covering the insertion section 2. A distal end of the sheath 55 is fixed to the inner surface of the guide hole 52 of the cup-shaped member 50. A proximal end of the sheath 55 is fixed to the inner tube member 47 by a beam member 55a.

The manipulation section 60 shown in FIGS. 15 and 16 are provided at the proximal portion of the incision instrument 1A. The manipulation section 60 is configured to perform advance and retract manipulation of the insertion section 2, and rotational manipulation of rotating the entire incision instrument 1A about the centerline of the outer tube member 42 serving as a rotational center. The manipulation section 60 includes the shaft section 61 and the slider 66. The shaft section 61 extends from the proximal end toward the proximal side of the connecting member 48. The slider 66 is attached to the shaft section 61.

The shaft section 61 has substantially a rod shape which is capable of gripping by an operator. The shaft section 61 includes a substantially tubular shaft body 62, a ring 63 and serrated sections 64. The ring 63 is formed at the proximal end of the shaft body 62. The serrated sections 64 are disposed at the outer surface of the shaft body 62 side by side in a longitudinal direction of the shaft body 62.

The shaft body 62 has a substantially tubular shape into which the proximal portion of the second conductive member 8 is inserted. A penetration hole 62a configured to connect the shaft body 62 and the slider 66 is installed in the shaft body 62 to extend in the longitudinal direction of the shaft body 62.

The distal end of the shaft body 62 is inserted into the hole 48a of the connecting member 48. A proximal end of the first insulating member 3 of the insertion section 2 is fixed to the distal end of the shaft body 62. The centerline of the shaft body 62 is set to be coaxially with the centerline of the inner tube member 47. For this reason, as the shaft body 62 is rotated about the centerline serving as a rotational center, the inner tube member 47 and the abutting section 49 fixed to the inner tube member 47 are rotated about the centerline of the inner tube member 47 serving as a rotational center.

The ring 63 has an annular shape such that a centerline extends in a direction perpendicular to the centerline of the shaft body 62 at the proximal end of the shaft body 62. The ring 63 has an inner dimension such that an operator's finger is insertable. An outer diameter of the ring 63 is larger than the diameter of the shaft body 62. The ring 63 may be held by the operator's finger when the shaft body 62 is rotated and manipulated about the centerline of the shaft body 62.

The serrated section 64 is constituted by a plurality of protrusions 65 protruding outward in the radial direction of the shaft body 62 in the outer surface of the shaft body 62. The serrated section 64 is integrally formed with the shaft body 62. In the embodiment, the plurality of protrusions 65 that constitute the serrated section 64 are disposed in the outer circumferential surface of the shaft body 62 along an opening end of the penetration hole 62a formed in the shaft body 62. In the embodiment, the serrated sections 64 are disposed at two positions opposite to each other interposing a central axis of the shaft body 62 and are disposed so as to protrude to an opposite direction with each other. The plurality of protrusions 65 constituting the serrated section 64 are engaged with a convex section 68 of the slider 66 (to be described below). As the convex section 68 is disposed between a set of neighboring protrusions 65 of the plurality of protrusions 65 constituting the serrated section 64, the position of the slider 66 in the serrated section 64 can be maintained. The slider 66 is configured to move in the serrated section 64 with respect to the shaft body 62 in the longitudinal direction of the shaft body 62 when an external force is applied to the ring 63 by the operator such that the convex section 68 of the slider 66 climbs over the protrusions 65 of the serrated section 64.

The slider 66 is a member which is configured to advance and retract with respect to the shaft body 62 in the longitudinal direction of the shaft body 62. The slider 66 is provided for advancing and retracting the second conductive member 8 with respect to the first insulating member 3. The slider 66 includes a tubular body 67, the convex section 68 and the connector 69. The shaft body 62 is inserted through the tubular body 67. The convex section 68 is formed at the inner surface of the tubular body 67. The connector 69 is fixed to the proximal end of the second conductive member 8 and fixed to the tubular body 67.

As shown in FIG. 16, a penetration hole 67*a* slightly larger than the outer diameter of the shaft body 62 is formed at the tubular body 67. The inner diameter of the tubular body 67 is smaller than the outer diameter of the ring 63 shown in FIG. 15. The tubular body 67 advances and retracts with respect to the shaft body 62 by a manual operation of the operator. The outer surface of the tubular body 67 may be configured such that the operator's finger can be hooked.

The convex section 68 protrudes inward from the inner surface of the penetration hole 67*a* formed in the slider 66. For example, the convex section 68 is pressed against by a biasing means such as a spring or the like.

As shown in FIGS. 15 and 16, the connector 69 is provided for attaching the cord C connected to the high frequency power supply apparatus 30. The connector 69 is fixed to a hole which connects the outer surface of the tubular body 67 and the inner surface of the penetration hole 67*a* of the tubular body 67, and protrudes into the penetration hole 67*a* of the tubular body 67. A portion of the connector 69 protruding into the penetration hole 67*a* of the tubular body 67 of the slider 66 extends to a centerline portion of the shaft body 62 through the penetration hole 62*a* of the shaft body 62, and is fixed to the proximal end of the second conductive member 8. For this reason, when the slider 66 advances and retracts with respect to the shaft body 62 in the longitudinal direction of the shaft body 62, the slider 66 and the connector 69 integrally advance and retract to cause the second conductive member 8 to advance and retract with respect to the shaft body 62 in the longitudinal direction of the shaft body 62.

Next, an action of the incision instrument 1A according to the embodiment will be described.

Specifically, the total laparoscopic hysterectomy (TLH) using the incision instrument 1A according to the embodiment is shown as an example. In the total laparoscopic hysterectomy, the womb is separated by the treatment of incising the vaginal canal after the treatment with respect to the plurality of ligaments, blood vessels, adhered tissues and adnexa that support the womb is performed.

In the embodiment, the womb is dissected from the vaginal canal at a dissection line where is the boundary portion between the womb neck area and the vaginal canal serving. First, the treatments for the plurality of ligaments supporting the womb, blood vessels, adhered tissues and adnexa are performed by known procedures. These procedures are performed under the laparoscopic observation. In addition, according to necessity, the womb manipulator may be inserted into the womb from the vaginal canal to adjust the position of the womb.

The incision instrument 1A according to the embodiment is prepared in a state in which the high frequency power supply apparatus 30 is connected to the connector 69. The slider 66 of the manipulation section 60 is disposed at the proximal portion of the shaft section 61. The distal end of the second conductive member 8 is disposed closer to the proximal side than the opening section 12 of the second insulating member 11. The shaft body 62 of the manipulation section 60 is disposed at the proximal side of the connecting member 48. The distal end of the insertion section 2 is disposed closer to the proximal side than the distal end of the sheath 55. Upon use of the incision instrument 1A, first, the operator inserts the incision instrument 1A according to the embodiment into the vaginal canal 110. As shown in FIG. 17, the abutting section 49 side of the incision instrument 1A is inserted into the vaginal canal 110 until the abutting section 49 comes in contact with the first portion 101.

In the abutting section 49, the concave surface section 51 of the cup-shaped member 50 comes in contact with the uterine cervix 102 so as to cover the first portion 101. The guide hole 52 formed in the cup-shaped member 50 supports the insertion section 2 via the sheath 55 such that the second conductive member 8 can protrude in a direction substantially along the outer surface of the uterine cervix 102 toward a direction inclined with respect to the centerline of the inner tube member 47. The protrusion direction of the distal portion of the second conductive member 8 is a linear direction crossing the boundary portion between the uterine cervix 102 and the vaginal canal 110.

The distal end of the positioning member 53 is inserted into the orifice of the uterus 103.

Figure 18:
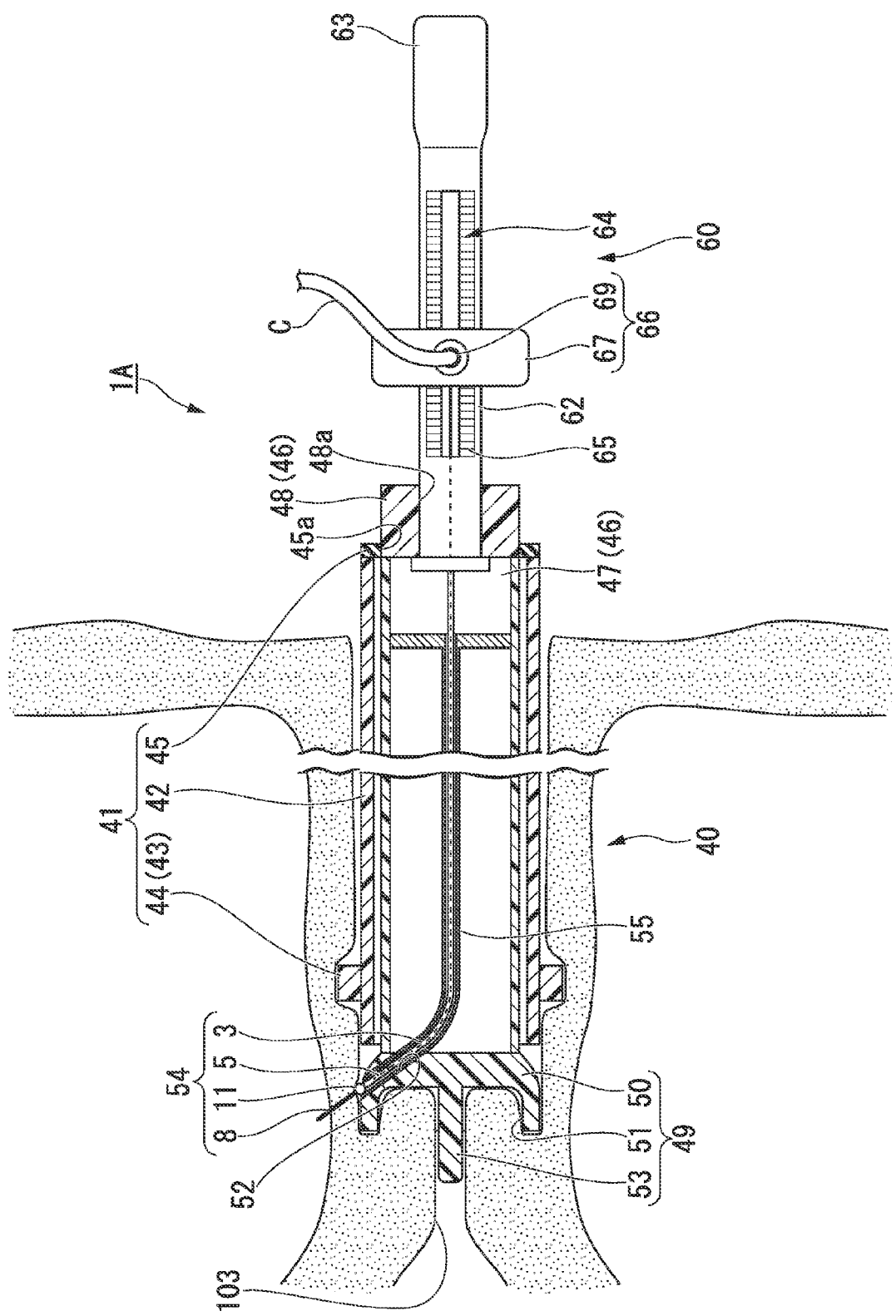
FIG. 18 is a view used to explain the action of the incision instrument according to the second embodiment of the present invention.

The operator checks that another tissue does not come in contact with the vicinity of the boundary portion between the uterine cervix 102 and the vaginal canal 110 under the laparoscopic observation. After that, the high frequency current is applied to the second conductive member 8 from the high frequency power supply apparatus 30 via the connector 69. Further, as shown in FIG. 18, the operator moves the slider 66 toward the distal side of the shaft body 62. As a result, the second conductive member 8 protrudes from the opening section 12 of the second insulating member 11 toward the distal side. In the embodiment, the protrusion length of the second conductive member 8 from the opening section 12 is determined according to the position at which the convex section 68 is locked in the serrated section 64. Since the convex section 68 of the slider 66 and the protrusions 65 of the serrated section 64 of the shaft body 62 are engaged with each other, the position of the slider 66 is maintained at a position at which the operator stops the manipulation of the slider 66. Accordingly, even when the operator separates his/her finger from the slider 66, the second conductive member 8 is held at the protrusion length at which the second conductive member 8 can penetrate the vaginal wall 111.

The distal end of the second conductive member 8 penetrates the vaginal wall 111 at the boundary portion between the uterine cervix 102 and the vaginal canal 110 and penetrates the vaginal wall 111 to reach the inside of the abdominal cavity. A position of the distal end of the second conductive member 8 can be recognized by the laparoscope. When the second conductive member 8 cannot be recognized under the laparoscopic observation, the thickness of the vaginal canal 110 may be smaller than the protrusion length of the second conductive member 8. For this reason, according to necessity, the second conductive member 8 is adjusted to penetrate the vaginal wall 111 by moving the slider 66 with respect to the shaft body 62.

After the second conductive member 8 penetrates the vaginal wall 111, the operator moves the slider 66 toward the proximal side of the shaft body 62 to house the second conductive member 8 in the second insulating member 11 and bring the contact section 9 in contact with the contact surface 7 (see FIG. 11) like the first embodiment. Accordingly, the high frequency current can be supplied to the first conductive member 5 from the second conductive member 8 via the contact section 9. A conduction state between the contact section 9 and the contact surface 7 is maintained by locking the slider 66 onto the serrated section 64.

Figure 19:
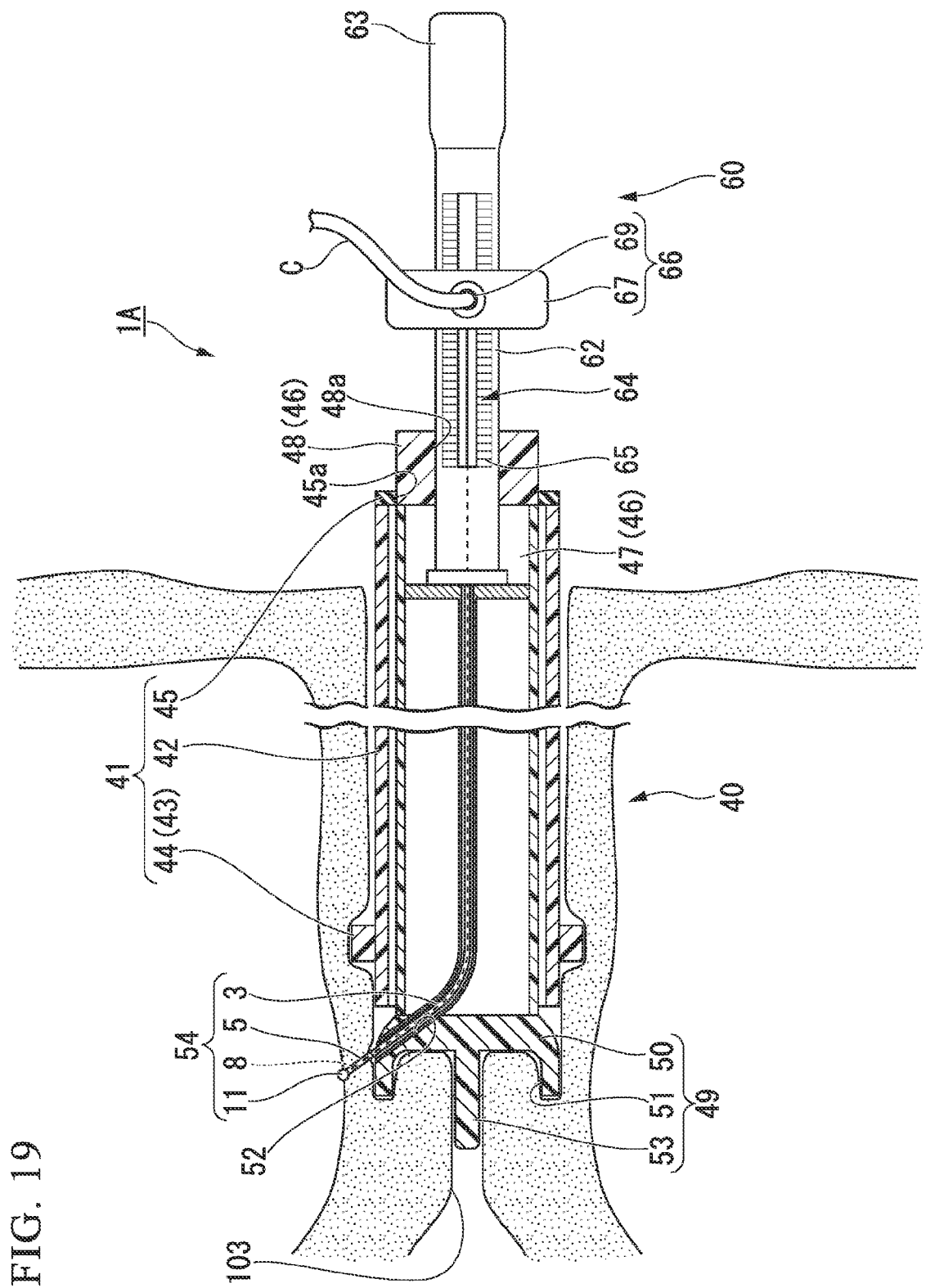
FIG. 19 is a view used to explain the action of the incision instrument according to the second embodiment of the present invention.

Next, the operator moves the shaft body 62 toward the distal side with respect to the connecting member 48, thereby the second insulating member 11 is inserted into the penetration hole formed by the second conductive member 8 as shown in FIG. 19. Since the second insulating member 11 has a larger diameter than the first conductive member 5, when the second insulating member 11 is inserted into the penetration hole 104 of the vaginal wall 111, the second insulating member 11 is locked to the vaginal wall 111 such that the second insulating member 11 cannot easily return into the vagina.

The operator rotates the shaft body 62 of the manipulation section 60 about the centerline of the shaft body 62 serving as a rotational center while applying the high frequency current to the first conductive member 5. The rotational direction of the shaft body 62 is not particularly limited. As a result, the shaft body 62 rotates the cup-shaped member 50 via the connecting member 48 and the inner tube member 47. Since the distal end of the positioning member 53 is inserted into the orifice of the uterus 103, the cup-shaped member 50 rotates about the orifice of the uterus 103 serving as a rotational center. The outer tube member 42 is not rotated by rotational manipulation of the shaft body 62. For this reason, in a state in which the locking section 43 provided at the outer tube member 42 is locked to the inner surface of the vaginal wall 111, the vaginal wall 111 is incised while the first conductive member 5 is rotated in the circumferential direction of the vaginal wall 111. At that time, a surface of the second insulating member 11 directed toward the proximal side of the second insulating member 11 continuously guides the vaginal canal 110 to the outer circumferential surface of the first conductive member 5. As a result, the first conductive member 5 rotates about the centerline of the vaginal canal 110 without deviation from the dissection line in the vaginal canal 110.

Figure 20:
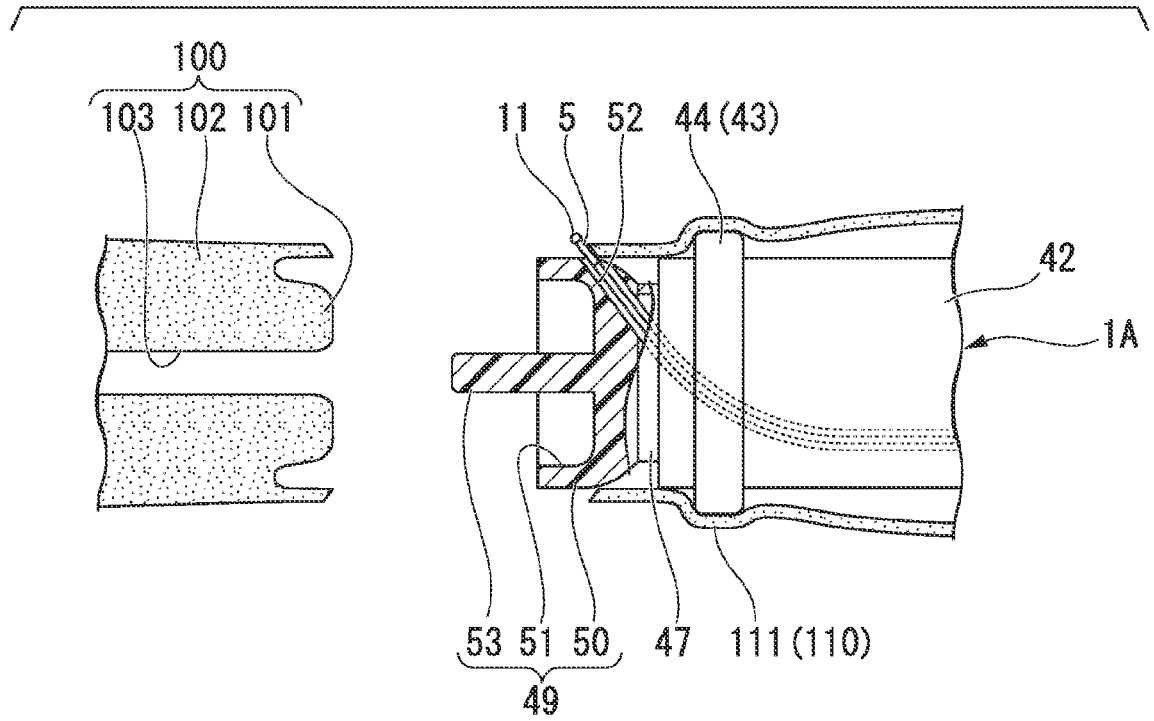
FIG. 20 is a view used to explain the action of the incision instrument according to the second embodiment of the present invention.

The first conductive member 5 returns to a penetration area of the vaginal wall 111 when the first conductive member 5 is rotated once in the circumferential direction of the vaginal wall 111. That is, as shown in FIG. 20, the vaginal wall 111 is dissected along the entire circumference using the boundary portion between the uterine cervix 102 and the vaginal canal 110 as a dissection line. Accordingly, the womb 100 is dissected from the vaginal canal 110.

After the womb 100 is dissected from the vaginal canal 110, the womb 100 is extracted from the body by the known procedures through the vaginal canal 110 or an incision region formed in the abdominal wall.

In the incision instrument 1A according to the embodiment, the first conductive member 5 being penetrating the vaginal canal 110 can be rotated about the centerlines of the outer tube member 42 and the inner tube member 47 serving as a rotational center by rotating the shaft body 62 of the manipulation section 60 about the centerline of the shaft body 62 serving as a rotational center. The outer surface of the outer tube member 42 comes in contact with the inner surface of the vaginal canal 110, and the vaginal canal 110 has a tubular shape having a center on the centerline of the outer tube member 42. For this reason, in the vaginal canal 110 formed in a tubular shape, the first conductive member 5 can dissect the vaginal canal 110 along a circular dissection line extending in the circumferential direction of the vaginal canal 110 in a surface perpendicular to the centerline of the vaginal canal 110 by rotating the first conductive member 5 about the centerlines of the outer tube member 42 and the inner tube member 47 serving as a rotational center.

In this way, according to the incision instrument 1A according to the embodiment, the vaginal canal 110 can be dissected along an ideal dissection line in the boundary portion between the uterine cervix 102 and the vaginal canal 110. Further, after the second conductive member 8 penetrates the vaginal canal 110, the all layer incision of the vaginal canal 110 is performed by the first conductive member 5 having the second insulating member 11 formed at the distal end. As the result, the distal end of the first conductive member 5 does not come in erroneous contact with another biological tissue where is not scheduled to be incised. As a result, even in a state in which the dissection line cannot be clearly checked by the laparoscopic observation, a possibility of incision of unnecessary areas except for the dissection line can be limited to a low level.

As the manipulation for dissection of the vaginal canal 110, only the shaft body 62 is rotated about the centerline of the shaft body 62 serving as a rotational center in a state in which the high frequency current is applied to the first conductive member 5, cooperative manipulation of the plurality of tools is not needed. That is, since the positioning in which a position of the first conductive member 5 is matched to the dissection line is performed by holding the vaginal canal 110 by the outer tube member 42, the operator can dissect the vaginal wall 111 along the ideal dissection line by only performing the rotational manipulation of the shaft body 62.

According to the incision instrument 1A of the embodiment, the distal portion of the insertion section 2 is rotated so that the first conductive member 5 performs the all layer incision from a site where the second conductive member 8 penetrates the vaginal wall 111 and returns to the site. For this reason, position adjustment of the distal portion of the insertion section 2 during the dissection operation is easily performed, and workability is improved.

According to the incision instrument 1A of the embodiment, the distal end section of the second conductive member 8 advances and retracts in a direction crossing the centerline of the vaginal canal 110, and the second conductive member 8 penetrates the vaginal wall 111 to move outward in the radial direction of the vaginal canal 110 toward the distal side. For this reason, in comparison with the case in which the second conductive member 8 protrudes in a direction perpendicular to the centerline of the vaginal canal 110, an excision quantity of the vaginal canal 110 after the all layer incision using the first conductive member 5 after the penetration is reduced, and the vaginal canal 110 can remain. Further, when the second conductive member 8 penetrates the vaginal canal 110 or in a process of dissecting the vaginal canal 110 using the first conductive member 5 throughout the entire circumference, the first conductive member 5 or the second conductive member 8 cannot easily come in contact with the uterine cervix 102. In addition, in comparison with the case in which the second conductive member 8 protrudes in a direction perpendicular to the centerline of the vaginal canal 110, the possibility of erroneous contact of the distal end of the second conductive member 8 with another biological tissue in the abdominal cavity can be limited to a low level.

In a state in which the concave surface section 51 of the cup-shaped member 50 is in contact with the first portion 101, the cup-shaped member 50 is stabilized in a state in which the cup-shaped member 50 covers the first portion 101. For this reason, the operator can easily penetrate the boundary portion between the uterine cervix 102 and the vaginal canal 110 with the second conductive member 8 by only moving the slider 66 toward the distal side in a state in which the concave surface section 51 of the cup-shaped member 50 is pressed against the first portion 101.

In a state in which the concave surface section 51 of the cup-shaped member 50 is in contact with the first portion 101, the cup-shaped member 50 is rotatable about the first portion 101 serving as a rotational center. For this reason, the operator can easily rotate the first conductive member 5 along the dissection line of the boundary portion between the uterine cervix 102 and the vaginal canal 110 by only rotating the shaft body 62 in a state in which the concave surface section 51 of the cup-shaped member 50 is pressed against the first portion 101.

Since the guide hole 52 configured to support the insertion section 2 via the sheath 55 is formed at the cup-shaped member 50, the distal end of the second conductive member 8 easily arrives at the boundary portion between the uterine cervix 102 and the vaginal canal 110.

According to the incision instrument 1A of the embodiment, since the positioning member 53 is provided, the cup-shaped member 50 is rotatable about the orifice of the uterus 103 serving as a rotational center. The positioning member 53 limits positional deviation of the womb 100 with respect to the vaginal canal 110 and positional deviation of the incision instrument 1A with respect to the womb 100. For this reason, positional deviation of the first conductive member 5 from the dissection line in a dissection process of the vaginal wall 111 using the first conductive member 5 can be limited.

The locking section 43 provided at the outer circumferential surface of the outer tube member 42 holds the vaginal wall 111 such that positional deviations of the outer tube member 42 and the vaginal wall 111 cannot easily occur. For this reason, twist of the vaginal canal 110 during the dissection operation cannot easily occur, and dissection of the vaginal wall 111 along the ideal dissection line becomes easy.

The airtight valve 45 which maintains an airtight state between the outer tube member 42 and the interior section 46 is installed at the exterior section 41. For this reason, a leakage of a gas from the gap between the outer tube member 42 and the interior section 46 is limited to a minimum level when pneumoperitoneum is performed to facilitate the procedure under the laparoscopic observation, and the outer tube member 42 and the interior section 46 can rotate about the centerline of the outer tube member 42 serving as a rotational center.

The locking section 43 provided at the outer tube member 42 can also limit the leakage of the gas filled in the abdominal cavity by the pneumoperitoneum.

Modified Example

Figure 21:
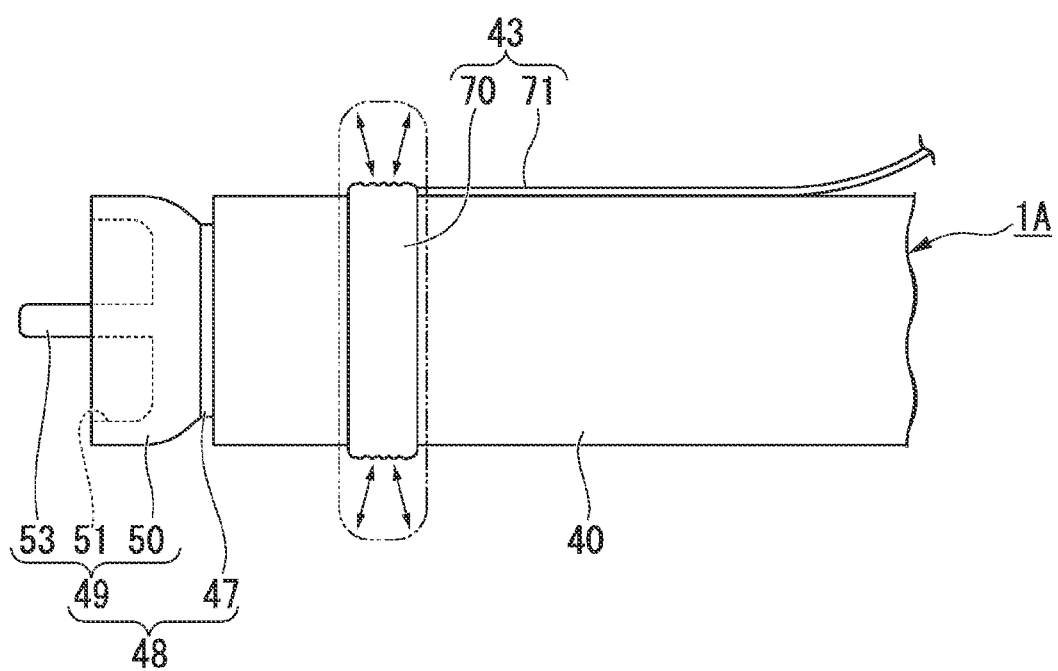
FIG. 21 is a side view showing a configuration of a modified example of the incision instrument according to the second embodiment of the present invention.

Next, a modified example of the embodiment will be described. FIG. 21 is a side view showing a configuration of a modified example of the incision instrument 1A according to the embodiment.

The modified example has a configuration different from the embodiment in that the locking section 43 described in the embodiment has a balloon 70 and an air duct 71 as shown in FIG. 21, instead of the annular member 44.

The balloon 70 is formed in an annular shape about the centerline of the outer tube member 42 in the outer circumferential surface of the outer tube member 42, and fixed to the outer circumferential surface of the outer tube member 42. The balloon 70 has an expandable and contractile film form such that the balloon 70 can be expanded when a liquid or a gas is filled therein. When the liquid or the gas is filled in the balloon 70, the balloon 70 expands in a doughnut shape.

The air duct 71 is a tubular member having a distal end in communication with the inside of the balloon 70 and a proximal end connected to a pump. For example, the air duct 71 is fixed to the outer surface of the outer tube member 42. The air duct 71 may penetrate the outer tube member 42 to be pulled into the outer tube member 42, and may extend toward the proximal side of the main body section 40 through the gap between the outer tube member 42 and the interior section 46.

In the modified example, as the diameter of expanding the balloon 70 is adjusted, a pressing force of the balloon 70 with respect to the vaginal wall 111 is adjustable by adjusting the diameter of expanding the balloon 70. In the modified example, the outer tube member 42 can be locked to the vaginal wall 111 with an appropriate locking force corresponding to an individual difference of a patient.

Third Embodiment

Next, a third embodiment of the present invention will be described. Further, in the embodiments described below, the same reference numerals as the above-mentioned embodiments are designated by the same components as the components of the incision instrument 1 according to the above-mentioned first embodiment or the components of the incision instrument 1A according to the above-mentioned second embodiment in functions or structures, and an overlapping description of the embodiments will be omitted.

Figure 22:
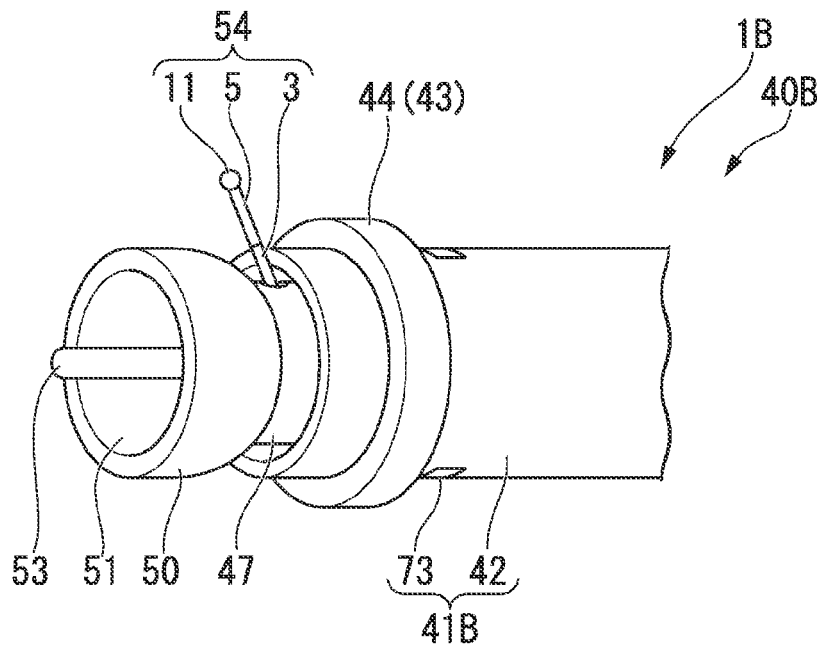
FIG. 22 is a perspective view showing a portion of an incision instrument according to a third embodiment of the present invention.
Figure 23:
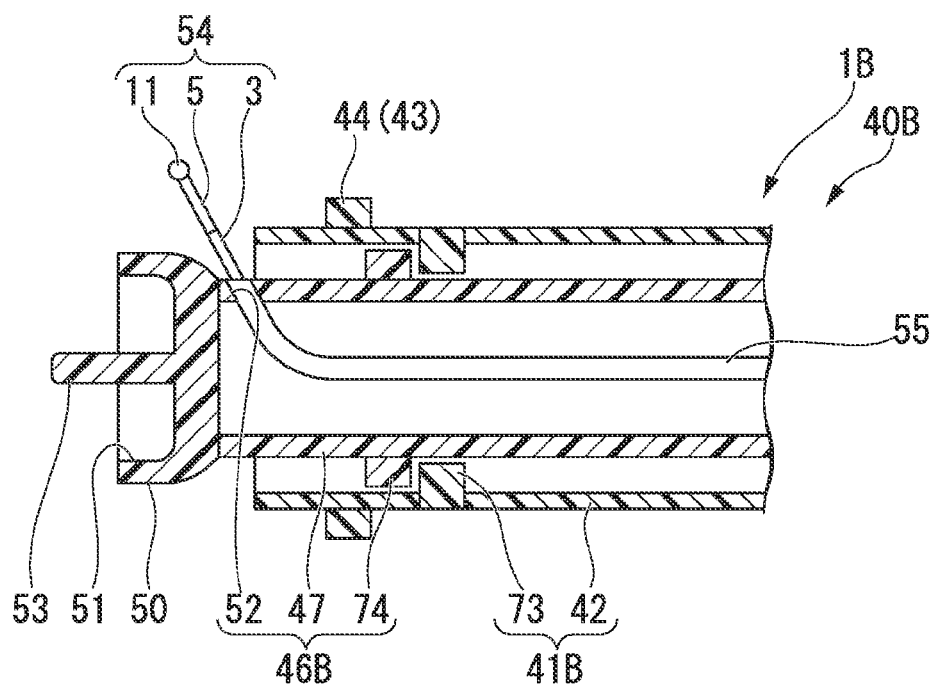
FIG. 23 is a cross-sectional view of a distal portion of the incision instrument according to the third embodiment of the present invention.

FIG. 22 is a perspective view showing a portion of an incision instrument 1B according to the embodiment. FIG. 23 is a cross-sectional view of a distal portion of the incision instrument 1B according to the embodiment.

As shown in FIGS. 22 and 23, the incision instrument 1B according to the embodiment includes a main body section 40B having a configuration different from the main body section 40 described in the second embodiment.

As shown in FIG. 23, the main body section 40B has an exterior section 41B and an interior section 46B. The exterior section 41B has a configuration different from the exterior section 41 of the second embodiment in that a first stopper 73 is provided at an inner circumferential surface of the outer tube member 42. The interior section 46B has a configuration different from the interior section 46 of the second embodiment in that a second stopper 74 is provided at an outer circumferential surface of the inner tube member 47 and the guide hole 52 is provided in the inner tube member 47 instead of the cup-shaped member 50. In the embodiment, the same incision section 54 and manipulation section 60 as the second embodiment are provided.

The first stopper 73 provided at the inner circumferential surface of the outer tube member 42 and extends in the circumferential direction of the outer tube member 42 throughout an entire circumference of the outer tube member 42. The first stopper 73 protrudes from the inner circumferential surface of the outer tube member 42 inward in the radial direction of the outer tube member 42.

The second stopper 74 provided at the outer circumferential surface of the inner tube member 47 and extends in the circumferential direction of the inner tube member 47 throughout the entire circumference of the inner tube member 47. The second stopper 74 protrudes from the outer circumferential surface of the inner tube member 47 outward in the radial direction of the inner tube member 47. There is a clearance between the outer circumferential surface of the second stopper 74 and the outer tube member 42. The clearance has a size such that the second stopper 74 is rotatable with respect to the outer tube member 42 about the centerline of the outer tube member 42 serving as a rotational center. The second stopper 74 is disposed closer to a distal side than the first stopper 73. The outer surface of the proximal side of the second stopper 74 can contact with the outer surface of the distal side of the first stopper 73.

The guide hole 52 formed in the inner tube member 47 guides the insertion section 2 in a direction inclined with respect to the centerline of the inner tube member 47, like the second embodiment. In a state in which the second stopper 74 contacts with the first stopper 73, there is a gap between the distal end of the outer tube member 42 and the interior section 46B such that the insertion section 2 can protrude. For this reason, in the embodiment, the insertion section 2 protrudes from the gap between the distal end of the outer tube member 42 and the interior section 46B.

Like the second embodiment, the incision instrument 1B according to the embodiment can also dissect the vaginal canal 110 along the ideal dissection line set to a boundary between the uterine cervix 102 and the vaginal canal 110.

Fourth Embodiment

Figure 24:
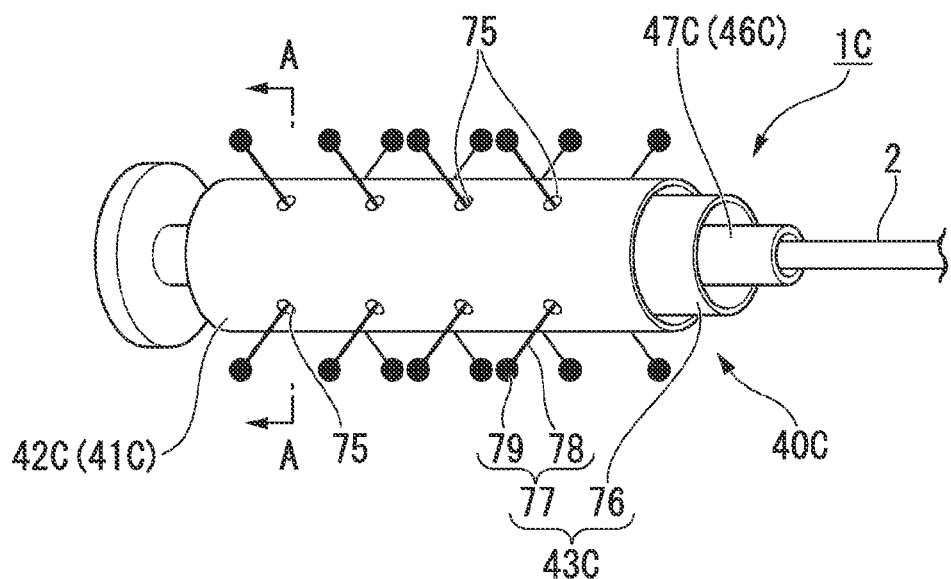
FIG. 24 is a perspective view showing an incision instrument according to a fourth embodiment of the present invention.
Figure 25:
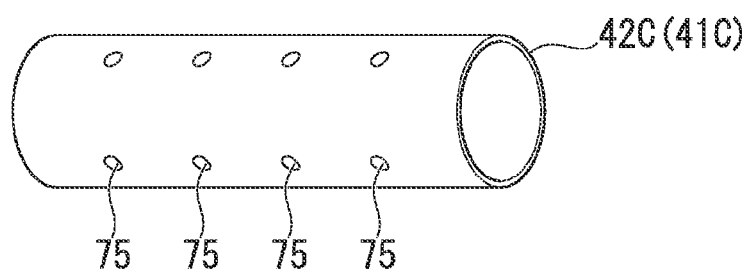
FIG. 25 is a perspective view showing an outer tube member of a vaginal wall incision section of the fourth embodiment of the present invention.
Figure 26:
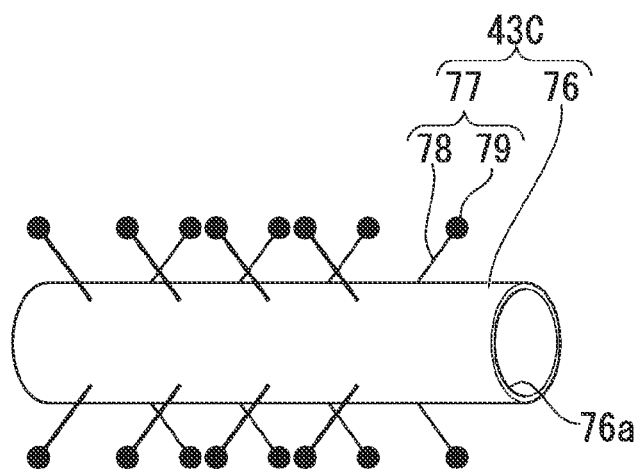
FIG. 26 is a perspective view showing an intermediate tube member of the incision instrument according to the fourth embodiment of the present invention.
Figure 27:
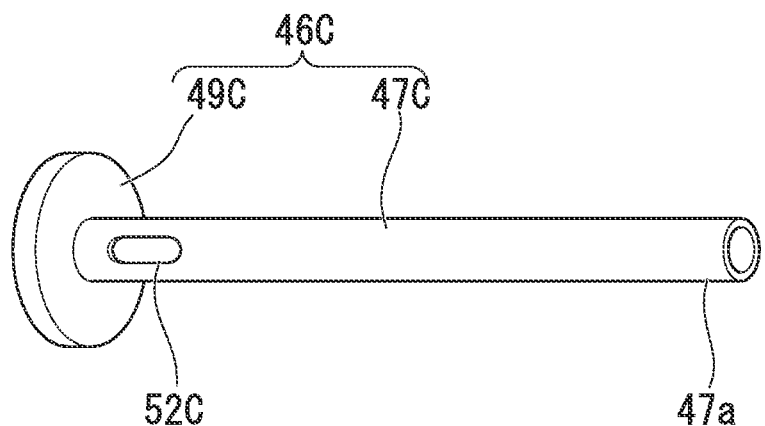
FIG. 27 is a perspective view showing an inner tube member of the incision instrument according to the fourth embodiment of the present invention.
Figure 28:
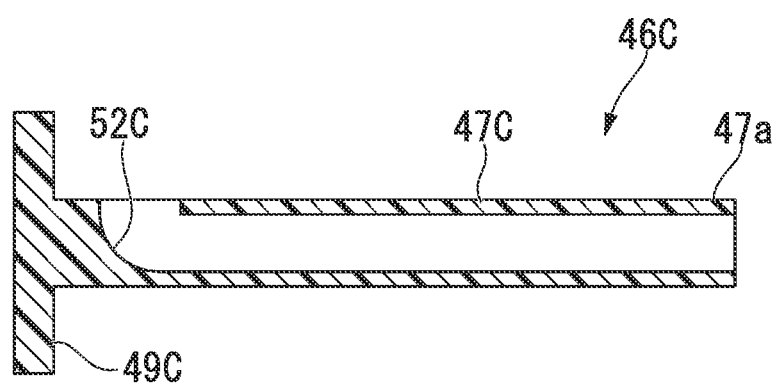
FIG. 28 is a cross-sectional view of the inner tube member of the incision instrument according to the fourth embodiment of the present invention.
Figure 29:
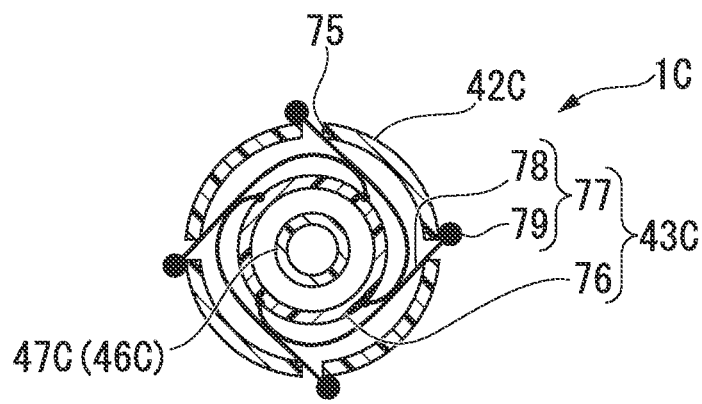
FIG. 29 is a cross-sectional view taken along line A-A of FIG. 24 as a view used to explain an action of the incision instrument according to the fourth embodiment of the present invention.
Figure 30:
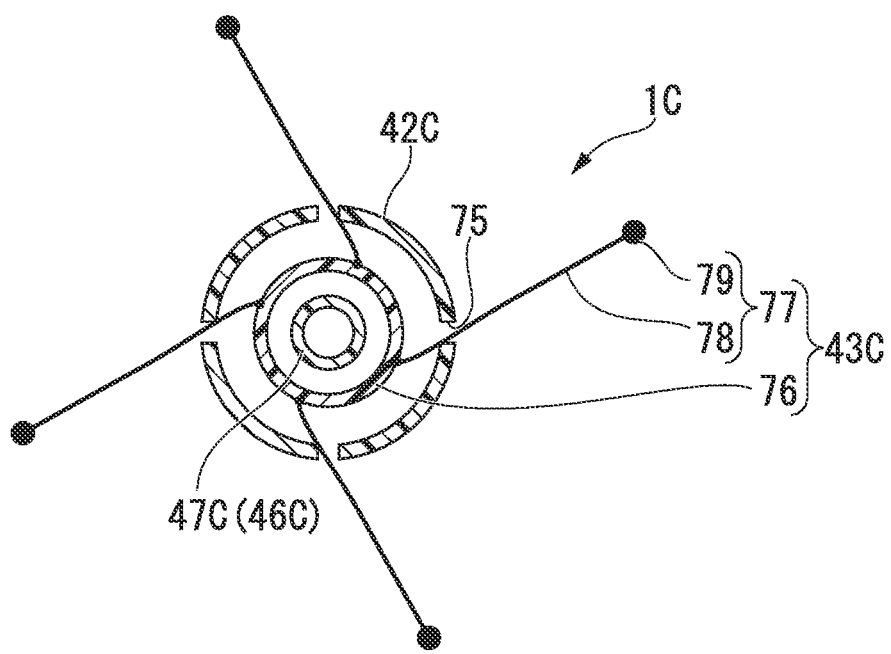
FIG. 30 is a cross-sectional view taken along line A-A of FIG. 24 as a view used to explain the action of the incision instrument according to the fourth embodiment of the present invention.

Next, a fourth embodiment of the present invention will be described. FIG. 24 is a general view showing an incision instrument 1C according to the embodiment. FIG. 25 is a perspective view showing an outer tube member 42C of the incision instrument according to the embodiment. FIG. 26 is a perspective view showing an intermediate tube member 76 of the incision instrument 1C according to the embodiment. FIG. 27 is a perspective view showing an inner tube member 47C of the incision instrument 1C according to the embodiment. FIG. 28 is a cross-sectional view showing the inner tube member 47C of the incision instrument 1C according to the embodiment. FIG. 29 is a cross-sectional view taken along line A-A of FIG. 24 as a view used to explain an action of the incision instrument 1C according to the embodiment. FIG. 30 is a cross-sectional view taken along line A-A of FIG. 24 as a view used to explain the action of the incision instrument 1C according to the embodiment.

As shown in FIG. 24, the incision instrument 1C according to the embodiment includes a main body section 40C having a configuration different from the main body section 40 described in the second embodiment. The incision instrument 1C according to the embodiment includes the incision instrument 1 described in the first embodiment instead of the incision section 54 described in the second embodiment.

The main body section 40C includes an exterior section 41C, a locking section 43C and an interior section 46C. The exterior section 41C has the outer tube member 42C having a shape different from the outer tube member 42 described in the second embodiment. The locking section 43C disposed in the exterior section 41C and has a configuration different from the locking section 43 described in the second embodiment. The interior section 46C has the inner tube member 47C disposed in the locking section 43C and has a configuration different from the interior section 46 described in the second embodiment.

As shown in FIG. 25, the outer tube member 42C of the exterior section 41C is a tubular member having a plurality of penetration holes 75 formed in an outer circumferential surface thereof. The plurality of penetration holes 75 formed in the outer circumferential surface of the outer tube member 42C are disposed at positions separated from each other in the circumferential direction of the outer tube member 42C, in parallel or randomly. The plurality of penetration holes 75 formed in the outer circumferential surface of the outer tube member 42C are disposed at positions separated from each other in the centerline direction of the outer tube member 42C.

As shown in FIG. 26, the locking section 43C includes the intermediate tube member 76 and a plurality of anchors 77. The intermediate tube member 76 is a tubular member disposed between the outer tube member 42C and the inner tube member 47C. The plurality of anchors 77 are fixed to an outer surface of the intermediate tube member 76.

The distal end of the intermediate tube member 76 is disposed at a position of the distal end of the outer tube member 42C or disposed closer to the proximal side than the distal end of the outer tube member 42C. A proximal end of the intermediate tube member 76 is disposed closer to the proximal side than the proximal end of the outer tube member 42C. The proximal portion of the intermediate tube member 76 is a first gripping section 76a held by an operator's hand and configured to manipulate rotation of the intermediate tube member 76. The inner tube member 47C is inserted into an inside of the intermediate tube member 76. A centerline of the intermediate tube member 76 is disposed substantially coaxially on both of a centerline of the outer tube member 42C and a centerline of the inner tube member 47C. The intermediate tube member 76 is rotatable with respect to the outer tube member 42C and the inner tube member 47C.

Each of the anchors 77 has a wire 78 and an end section member 79. The wire 78 is fixed to the outer circumferential surface of the intermediate tube member 76. The end section member 79 is fixed to an end section of the wire 78.

The wire 78 of the anchor 77 has a restoring force that can restore a substantially linear shape in a state in which an external force is not applied. For example, one end of the wire 78 of the anchor 77 is fixed to the intermediate tube member 76 through adhesion or the like to be inserted into the sidewall of the intermediate tube member 76. In the embodiment, the wire 78 of each of the anchors 77 is vertically fixed to the outer circumferential surface of the intermediate tube member 76.

The end section member 79 of the anchor 77 has a curved surface so as not to stimulate a mucous membrane. In the embodiment, the end section member 79 of the anchor 77 is a spherical member into which the end section of the wire 78 of the anchor 77 is inserted and fixed. An outer diameter of the end section member 79 is larger than an inner diameter of the penetration hole 75 formed in the outer circumferential surface of the outer tube member 42C.

As shown in FIG. 27, the interior section 46C has the inner tube member 47C and an abutting section 49C. The inner tube member 47C has a substantially cylindrical shape opened at a side of the distal portion and opened at the proximal end. The abutting section 49C is installed at the distal end of the inner tube member 47C. The proximal portion of the inner tube member 47C of the interior section 46C is a second gripping section 47a which is configured to be gripped and rotated about the centerline by an operator.

An opening in a side portion of a distal portion of the inner tube member 47C is an opening through which the insertion section 2 protrudes. That is, in the embodiment, the insertion section 2 is inserted into the distal side from a proximal end of the inner tube member 47C and the insertion section 2 protrudes from the opening in the side portion of the distal portion of the inner tube member 47C.

As shown in FIG. 28, the opening in the side portion of the distal portion of the inner tube member 47C has a curved surface or a flat surface inclined with respect to the centerline of the inner tube member 47 in the inner tube member 47C. Accordingly, the insertion section 2 inserted from the proximal side toward the distal side along the centerline of the inner tube member 47C protrudes in a direction inclined with respect to the centerline of the inner tube member 47C in the opening. In the embodiment, like the guide hole 52 described in the second embodiment, the opening in the side portion of the distal portion of the inner tube member 47C is a guide hole 52C configured to guide the distal end of the insertion section 2 toward the boundary portion between the uterine cervix and the vaginal canal.

The abutting section 49C has a disk shape formed along a plane perpendicular to the centerline of the inner tube member 47. The abutting section 49C of the embodiment may have a cup shape having a concave surface section that can contact with the uterine cervix like the second embodiment. The uterine cervix can contact with the outer surface of the distal side of the abutting section 49C. Like the concave surface section 51 described in the second embodiment, the distal end of the insertion section 2 can be positioned such that the insertion section 2 is directed toward the boundary portion between the uterine cervix and the vaginal canal.

Figure 31:
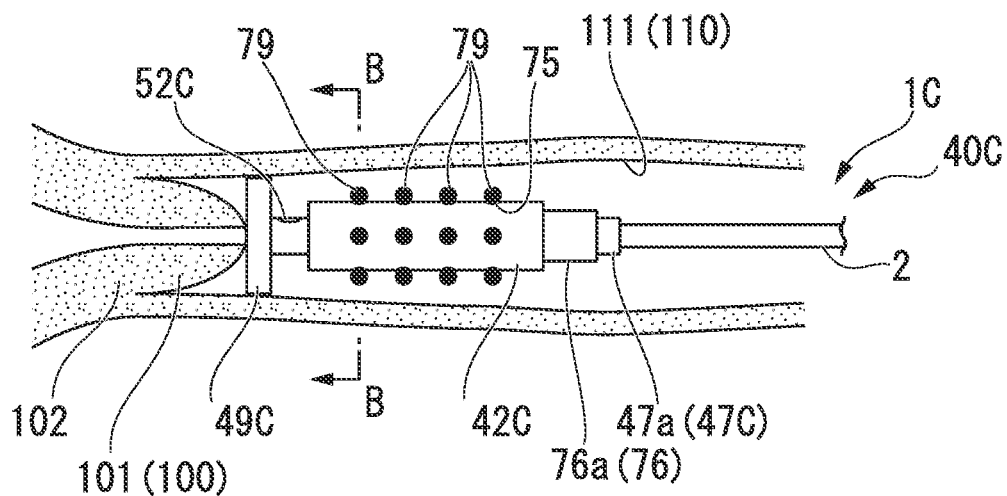
FIG. 31 is a view used to explain a procedure using the incision instrument according to the fourth embodiment of the present invention.
Figure 32:
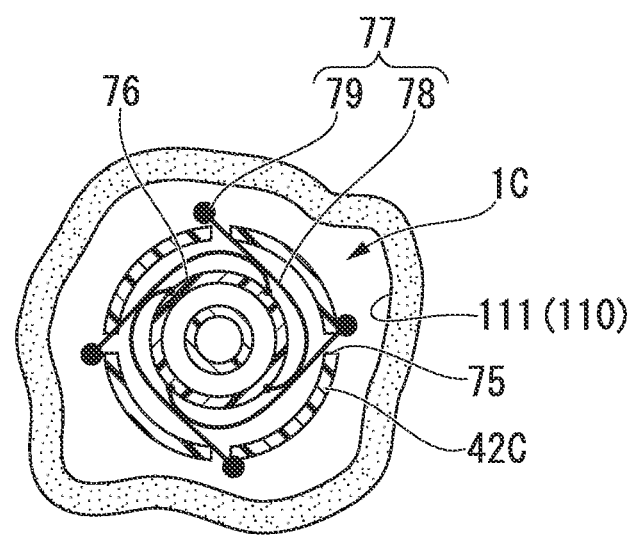
FIG. 32 is a cross-sectional view taken along line B-B of FIG. 31 as a view used to explain the procedure using the incision instrument according to the fourth embodiment of the present invention.
Figure 33:
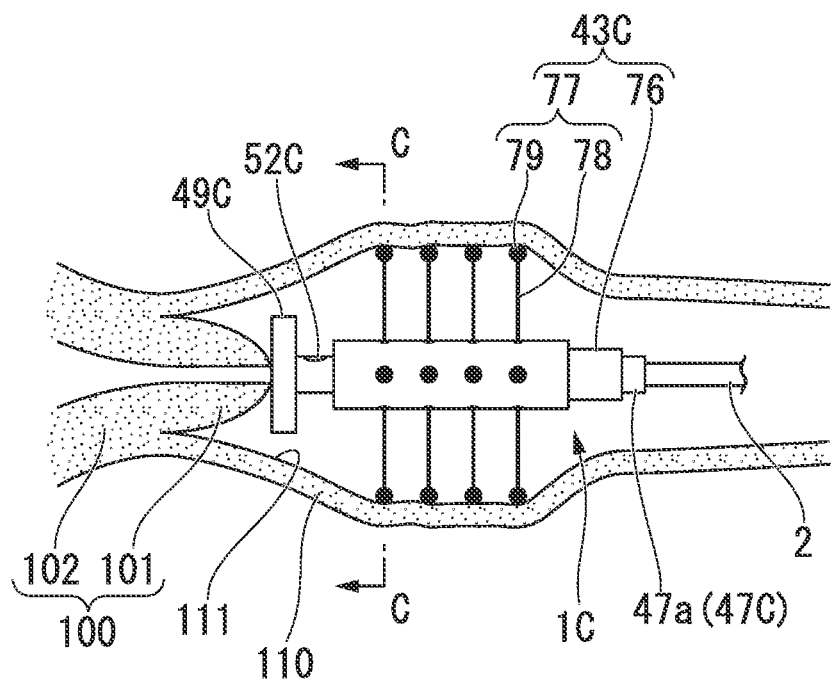
FIG. 33 is a view used to explain the procedure using the incision instrument according to the fourth embodiment of the present invention.
Figure 34:
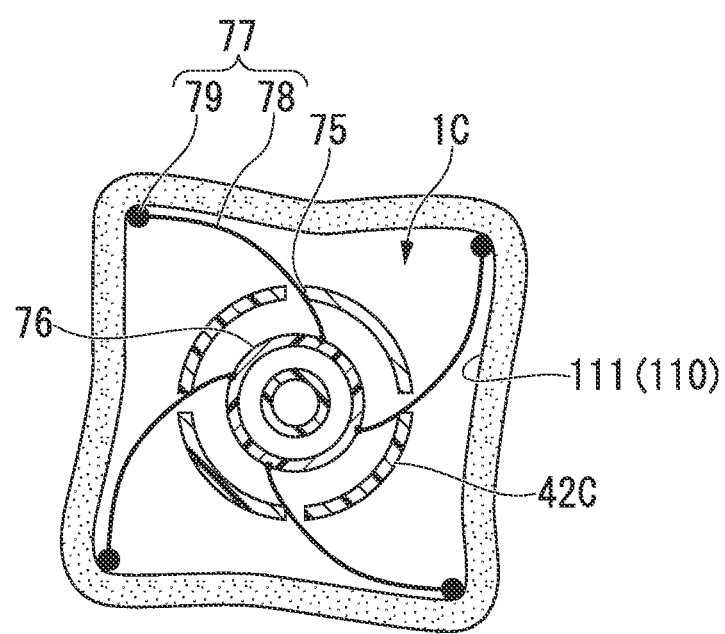
FIG. 34 is a cross-sectional view taken along line C-C of FIG. 33 as a view used to explain the procedure using the incision instrument according to the fourth embodiment of the present invention.
Figure 35:
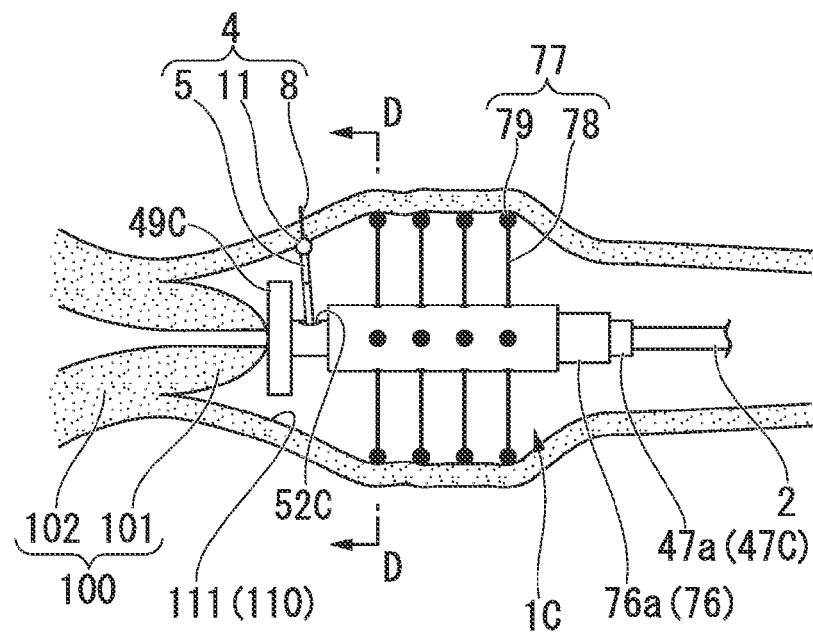
FIG. 35 is a view used to explain the procedure using the incision instrument according to the fourth embodiment of the present invention.
Figure 36:
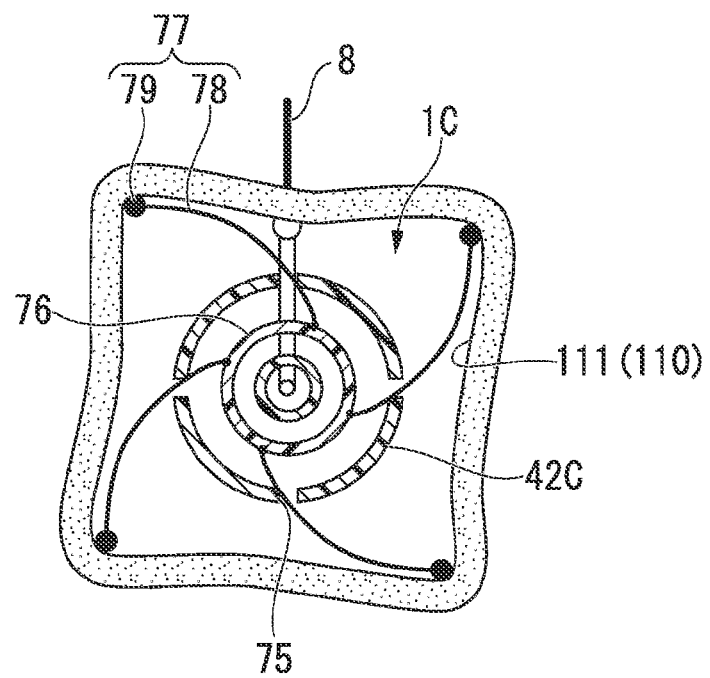
FIG. 36 is a cross-sectional view taken along line D-D of FIG. 35 as a view used to explain the procedure using the incision instrument according to the fourth embodiment of the present invention.
Figure 37:
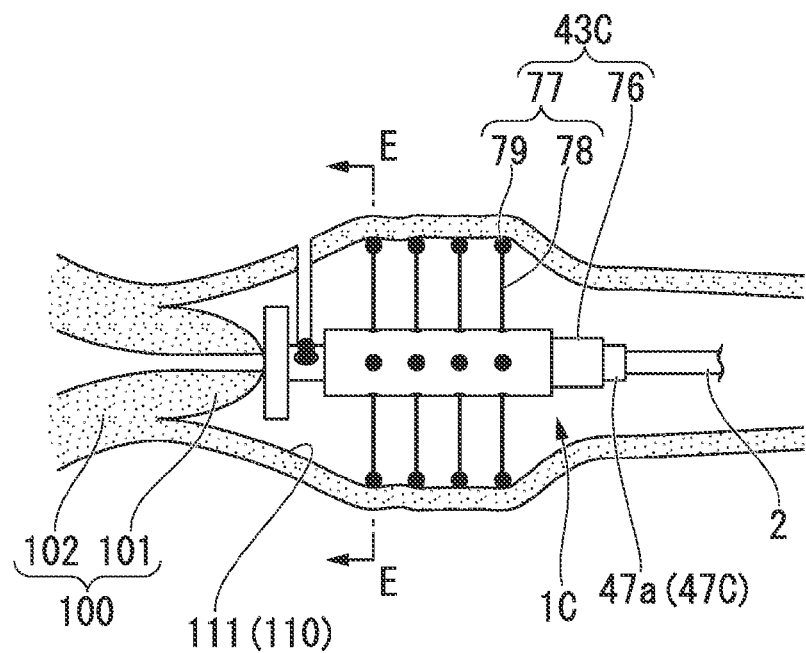
FIG. 37 is a view used to explain the procedure using the incision instrument according to the fourth embodiment of the present invention.
Figure 38:
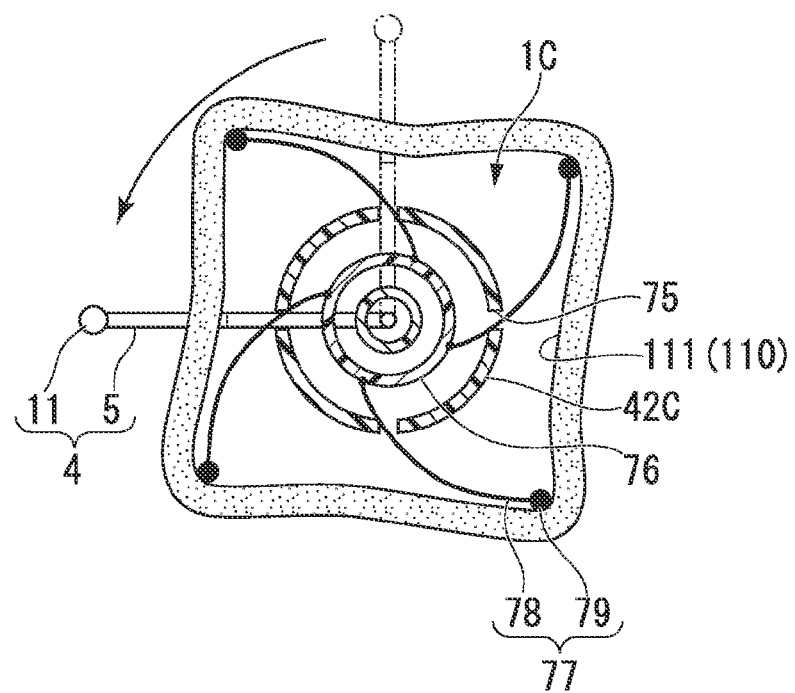
FIG. 38 is a cross-sectional view taken along line E-E of FIG. 37 as a view used to explain the procedure using the incision instrument according to the fourth embodiment of the present invention.

Next, an action of the incision instrument 1C according to the embodiment will be described. FIG. 31 is a view used to explain a procedure using the incision instrument 1C according to the embodiment. FIG. 32 is a cross-sectional view taken along line B-B of FIG. 31 as a view used to explain the procedure using the incision instrument 1C according to the embodiment. FIG. 33 is a view used to explain the procedure using the incision instrument 1C according to the embodiment. FIG. 34 is a cross-sectional view taken along line C-C of FIG. 33 as a view used to explain the procedure using the incision instrument 1C according to the embodiment. FIG. 35 is a view used to explain the procedure using the incision instrument 1C according to the embodiment. FIG. 36 is a cross-sectional view taken along line D-D of FIG. 35 as a view used to explain the procedure using the incision instrument 1C according to the embodiment. FIG. 37 is a view used to explain the procedure using the incision instrument 1C according to the embodiment. FIG. 38 is a cross-sectional view taken along line E-E of FIG. 37 as a view used to explain the procedure using the incision instrument 1C according to the embodiment.

In the embodiment, the wire 78 of the anchor 77 can enter or exit through the penetration hole 75 of the outer tube member 42C by manipulating the intermediate tube member 76 to rotate about the centerline serving as a rotational center with respect to the outer tube member 42C.

That is, as shown in FIGS. 31 and 32, when the main body section 40C is inserted into the vaginal canal 110, the wire 78 of the anchor 77 is wound on the outer circumferential surface of the intermediate tube member 76 (see FIG. 29). In a state in which insertion of the main body section 40C into the vaginal canal 110 is terminated and the abutting section 49C contacts with the first portion 101, the intermediate tube member 76 is rotated with respect to the outer tube member 42C to release the winding of the wire 78 of the anchors 77 on the intermediate tube member 76. As a result, the wire 78 of the anchor 77 is pushed toward the outside of the outer tube member 42C through the penetration hole 75 of the outer circumferential surface of the outer tube member 42C while being restored to the linear state (see FIG. 30). A restoring force is applied to the wire 78 of the anchor 77 to restore the linear state. For this reason, according to the magnitude of the restoring force of the wire 78, the wire 78 may be pushed toward the outside of the outer tube member 42C through the penetration hole 75 of the outer tube member 42C by only attenuating the force of winding the wire 78 on the intermediate tube member 76.

As a result, as shown in FIGS. 33 and 34, the wire 78 of the anchor 77 presses the vaginal wall 111 outward in the radial direction via the end section member 79. Like the locking section 43 described in the second embodiment, the outer tube member 42C is locked to the vaginal wall 111 by the frictional forces between each of the end section member 79 fixed to the wire 78 of the anchor 77 and the vaginal wall 111. When the wire 78 has the restoring force of pushing the wire 78 outward the outer tube member 42C through the penetration hole 75 of the outer tube member 42C by only attenuating the force of winding the wire 78 on the intermediate tube member 76, rotation of the intermediate tube member 76 is stopped at a position at which magnitude of each of the restoring force of the wire 78 is equal to a repulsive force from the vaginal wall 111.

After the outer tube member 42C is locked to the vaginal wall 111 by the anchor 77, as shown in FIGS. 35 and 36, the second conductive member 8 protrudes from the guide hole 52C serving as the opening in the side portion of the distal portion of the inner tube member 47. As a result, like the second embodiment, the distal end of the second conductive member 8 penetrates the vaginal wall 111, and the second conductive member 8 penetrates the vaginal wall 111 in the boundary portion between the uterine cervix 102 and the vaginal canal 110.

Next, the operator houses the second conductive member 8 in the second insulating member 11 like the second embodiment. Further, in a state in which the high frequency current is applied to the first conductive member 5, as shown in FIGS. 37 and 38, the second gripping section 47a is rotated about the centerline of the inner tube member 47C serving as a rotational center. Then, the first conductive member 5 rotates about the centerline of the vaginal canal 110 serving as a rotational center with respect to the vaginal wall 111 locked by the locking section 43C with respect to the outer tube member 42C. Accordingly, like the second embodiment, the first conductive member 5 dissects the vaginal wall 111 throughout the entire circumference.

Even in the embodiment, like the second embodiment, the vaginal wall 111 can be easily dissected along the ideal dissection line in the boundary between the uterine cervix 102 and the vaginal canal 110.

In the embodiment, manipulation of appropriately adjusting the length of the wire 78 of the anchor 77 can be easily performed by adjustment of a rotational amount of the intermediate tube member 76 with respect to the outer tube member 42C.

When each of the wire 78 has the restoring force with which the wire 78 is pushed toward the outside of the outer tube member 42C through the penetration hole 75 of the outer tube member 42C by only attenuating the force of winding the wire 78 on the intermediate tube member 76, rotation of the intermediate tube member 76 is stopped at the position at which the magnitude of each of the restoring force of the wire 78 is equal to the repulsive force from the vaginal wall 111. For this reason, the outer tube member 42 can be locked to the vaginal wall 111 with a constant locking force regardless of an individual difference of the patient.

Fifth Embodiment

Figure 39:
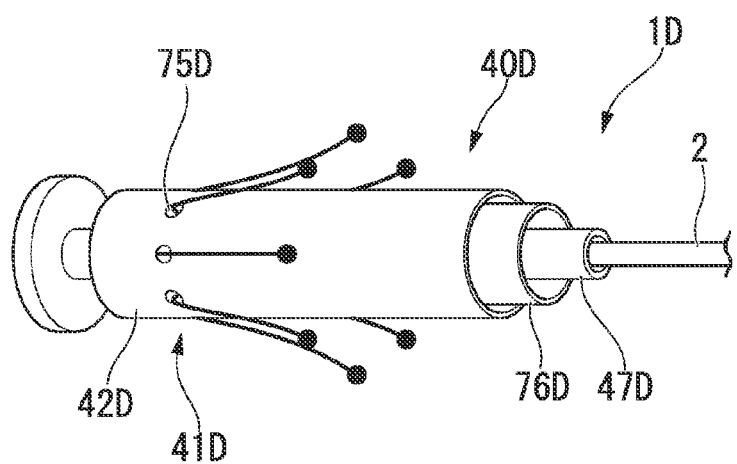
FIG. 39 is a perspective view showing an incision instrument according to a fifth embodiment of the present invention.
Figure 40:
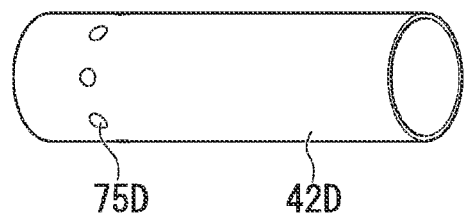
FIG. 40 is a perspective view showing an outer tube member of the incision instrument according to the fifth embodiment of the present invention.
Figure 41:
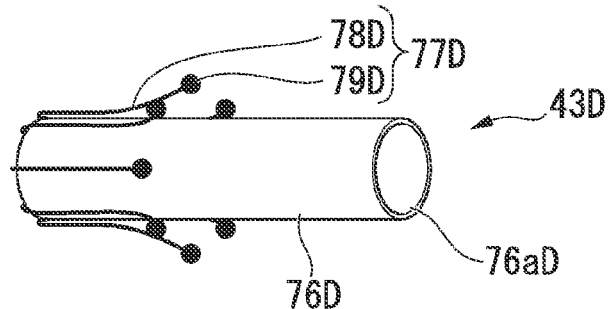
FIG. 41 is a perspective view showing an intermediate tube member of the incision instrument according to the fifth embodiment of the present invention.
Figure 42:
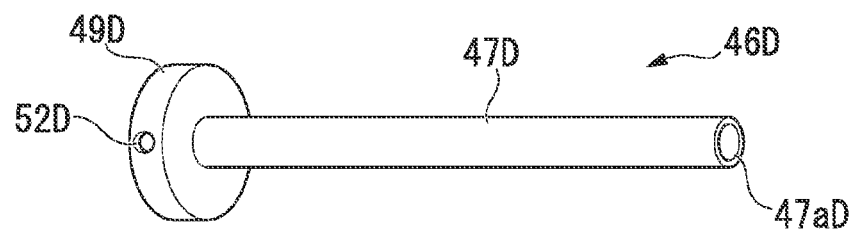
FIG. 42 is a perspective view showing an inner tube member of the incision instrument according to the fifth embodiment of the present invention.
Figure 43:
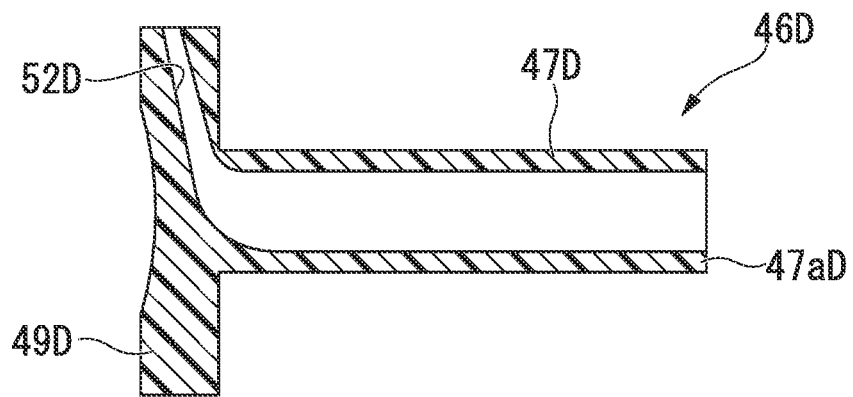
FIG. 43 is a cross-sectional view of the inner tube member of the incision instrument according to the fifth embodiment of the present invention.

Next, a fifth embodiment of the present invention will be described. FIG. 39 is a general view showing an incision instrument 1D according to the embodiment. FIG. 40 is a perspective view showing an outer tube member 42D of the incision instrument 1D according to the embodiment. FIG. 41 is a perspective view showing an intermediate tube member 76D of the incision instrument 1D according to the embodiment. FIG. 42 is a perspective view showing an inner tube member 47D of the incision instrument 1D according to the embodiment. FIG. 43 is a cross-sectional view of the inner tube member 47D of the incision instrument 1D according to the embodiment.

As shown in FIG. 39, the incision instrument 1D according to the embodiment includes a main body section 40D having a configuration different from the main body section 40 described in the second embodiment. The incision instrument 1D according to the embodiment includes the incision instrument 1 described in the first embodiment instead of the incision section 54 described in the second embodiment.

The main body section 40D includes an exterior section 41D, a locking section 43D and an interior section 46D having the inner tube member 47D. The exterior section 41D has the outer tube member 42D having a shape different from the outer tube member 42 described in the second embodiment. The locking section 43D is disposed in the exterior section 41D and has a configuration different from the locking section 43 described in the second embodiment. The interior section 46D has the inner tube member 47D disposed in the locking section 43D and having a configuration different from the interior section 46 described in the second embodiment.

As shown in FIG. 40, the outer tube member 42D of the exterior section 41D is a tubular member having a plurality of penetration holes 75D formed in an outer circumferential surface thereof. The plurality of penetration holes 75D of the outer tube member 42D are disposed at positions separated from each other in the circumferential direction of the outer tube member 42D, in parallel or randomly.

As shown in FIG. 41, the locking section 43D includes the intermediate tube member 76D and a plurality of anchors 77D. The intermediate tube member 76D is a tubular member disposed between the outer tube member 42D and the inner tube member 47D. The plurality of anchors 77D are fixed to the outer surface of the intermediate tube member 76D.

A distal end of the intermediate tube member 76D is disposed at a position of a distal end of the outer tube member 42D or disposed closer to the proximal side than the distal end of the outer tube member 42D. A proximal end of the intermediate tube member 76D is disposed closer to the proximal side than the proximal end of the outer tube member 42D. A proximal portion of the intermediate tube member 76D is a first gripping section 76aD configured to allow the operator to hold the intermediate tube member 76D with his/her hand to advance and retract the intermediate tube member 76D with respect to the outer tube member 42D. The inner tube member 47D is inserted into the inside of the intermediate tube member 76D.

A centerline of the intermediate tube member 76D is disposed substantially coaxially on both of a centerline of the outer tube member 42D and a centerline of the inner tube member 47D. The intermediate tube member 76D is able to advance and retract with respect to the outer tube member 42D in the centerline direction of the outer tube member 42D, and the intermediate tube member 76D is rotatable with respect to the inner tube member 47D about the centerline of the inner tube member 47D serving as a rotational center.

The anchor 77D has a wire 78D and an end section member 79D. The wire 78D is fixed to the outer circumferential surface of the intermediate tube member 76D. The end section member 79D is fixed to the end section of the wire 78D.

The wire 78D of the anchor 77D has a restoring force that enables restoration of a substantially linear shape in a state in which an external force is not applied. For example, one end of the wire 78D of the anchor 77D is inserted into the sidewall of the intermediate tube member 76D, or fixed to the intermediate tube member 76D through adhesion or the like along the outer circumferential surface of the intermediate tube member 76D. The wire 78D of the anchor 77D is fixed such that the intermediate tube member 76D is gradually inclined to be separated from the outer circumferential surface of the intermediate tube member 76D from the distal end of the intermediate tube member 76D toward the proximal side at the outer circumferential surface of the distal end of the intermediate tube member 76D.

The end section member 79D of the anchor 77D has a curved surface that does not stimulate a mucous membrane. In the embodiment, the end section member 79D of the anchor 77D is the same spherical member as the fourth embodiment. The outer diameter of the end section member 79D is larger than the inner diameter of the penetration hole 75D formed in the outer circumferential surface of the outer tube member 42D.

As shown in FIG. 42, the interior section 46D has a tubular inner tube member 47D and an abutting section 49D. The abutting section 49D is formed at the distal end of the inner tube member 47D and communicates with the inside of the inner tube member 47D. The proximal portion of the inner tube member 47D in the interior section 46D is a second gripping section 47aD which is configured to be gripped and rotated about the centerline by an operator.

As shown in FIG. 43, the guide hole 52D is formed in the abutting section 49D. The guide hole 52D is formed in order to protrude the insertion section 2, which is inserted from the proximal side of the inner tube member 47D toward the distal side, outward in the radial direction of the inner tube member 47D.

Like the guide hole 52 of the second embodiment, the guide hole 52D supports the second conductive member 8 such that the distal end of the second conductive member 8 of the insertion section 2 can penetrate the boundary portion between the uterine cervix and the vaginal canal. In the embodiment, the sheath 55 is not fixed to the inner surface of the guide hole 52D.

Like the fourth embodiment, the abutting section 49D has a disk shape along a plane perpendicular to the centerline of the inner tube member 47. Like the second embodiment, the abutting section 49D of the embodiment may have a cup shape having a concave surface section that can contact with the uterine cervix. The first portion 101 can contact with the outer surface of the distal side of the abutting section 49D, and like the concave surface section 51 described in the second embodiment, the second conductive member 8 can be positioned such that the second conductive member 8 is directed toward the boundary portion between the uterine cervix and the vaginal canal.

Figure 44:
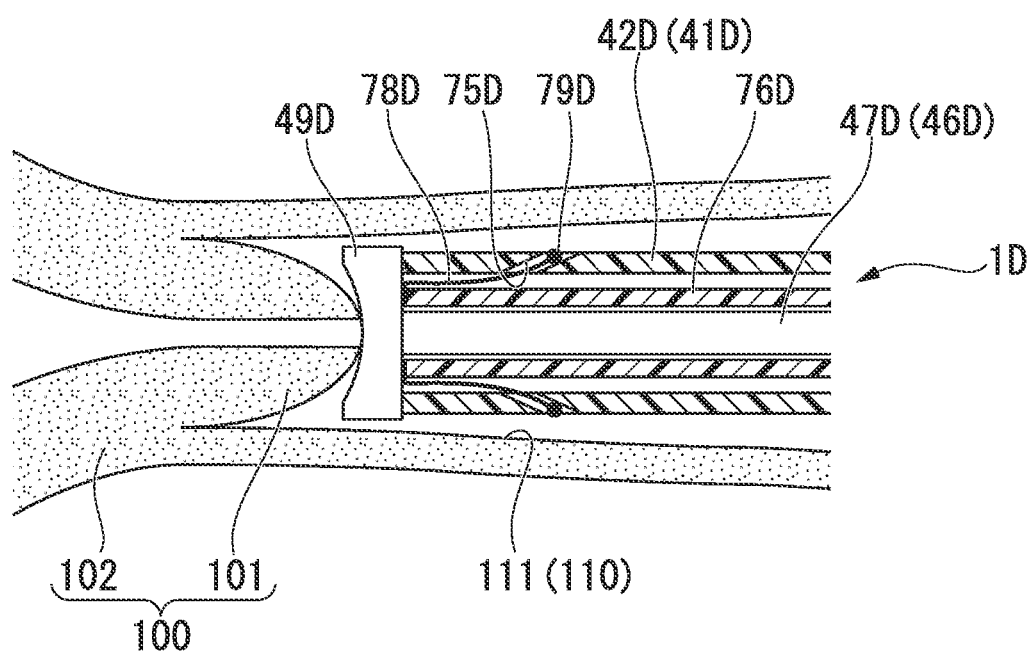
FIG. 44 is a view used to explain an action of the incision instrument according to the fifth embodiment of the present invention.
Figure 45:
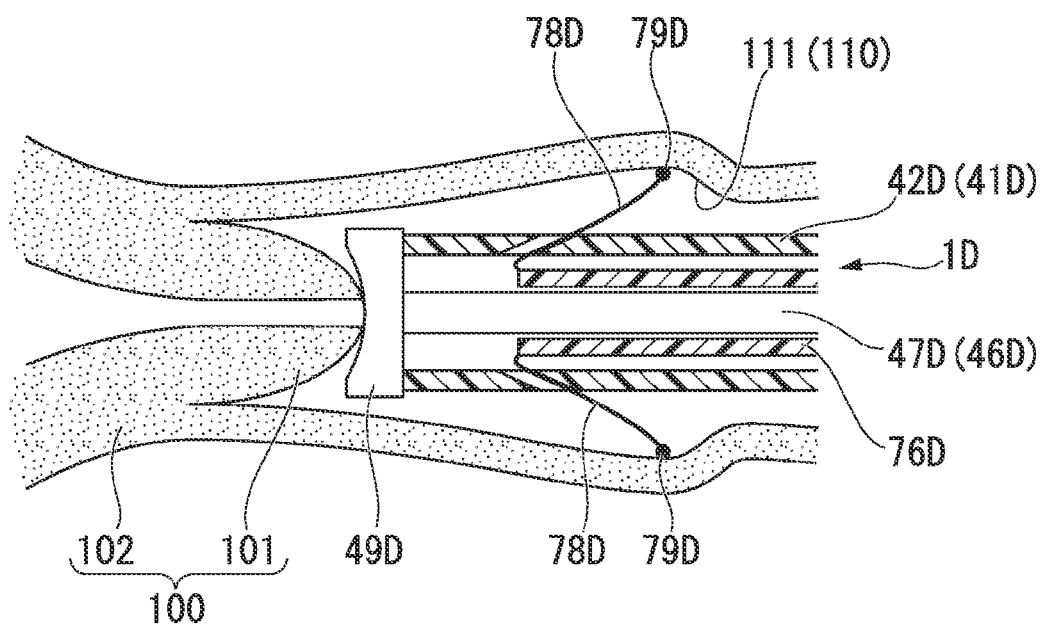
FIG. 45 is a view used to explain the action of the incision instrument according to the fifth embodiment of the present invention.

Next, an action of the incision instrument 1D according to the embodiment will be described. FIG. 44 is a view used to explain the action of the incision instrument 1D according to the embodiment. FIG. 45 is a view used to explain the action of the incision instrument 1D according to the embodiment. FIGS. 46 to 49 are views used to explain a procedure using the incision instrument 1D according to the embodiment.

As shown in FIGS. 44 and 45, in the embodiment, as the intermediate tube member 76D is manipulated with respect to the outer tube member 42D to advance and retract along the centerline, the wire 78D of the anchor 77D can enter and exit through the penetration hole 75D of the outer tube member 42D.

Figure 46:
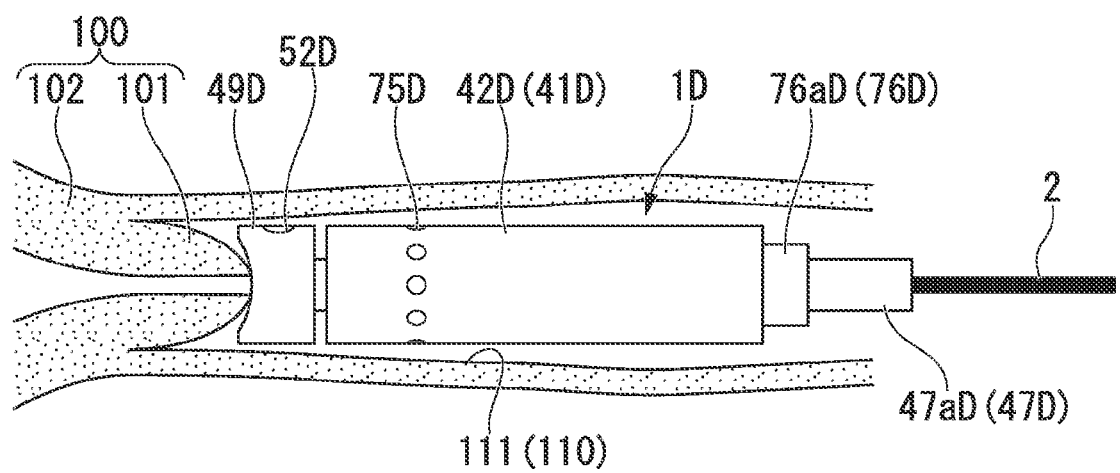
FIG. 46 is a view used to explain a procedure using the incision instrument according to the fifth embodiment of the present invention.
Figure 47:
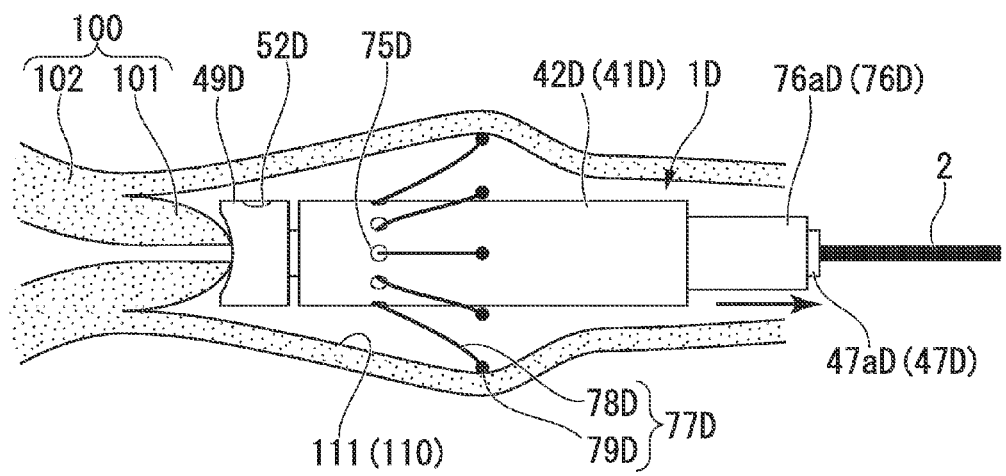
FIG. 47 is a view used to explain the procedure using the incision instrument according to the fifth embodiment of the present invention.
Figure 48:
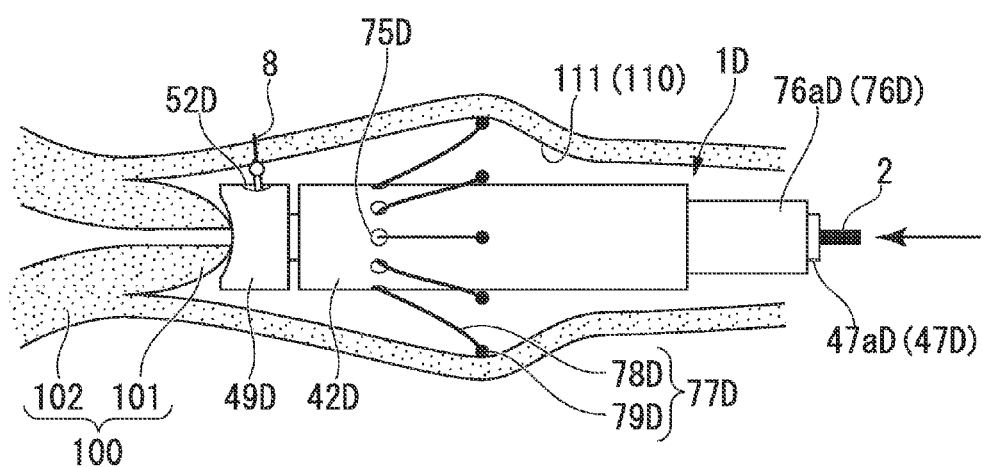
FIG. 48 is a view used to explain the procedure using the incision instrument according to the fifth embodiment of the present invention.

That is, when the main body section 40D is inserted into the vaginal canal 110 as shown in FIG. 46, the intermediate tube member 76D is pressed toward the distal side of the outer tube member 42D such that the wire 78D of the anchor 77D is housed in the gap between the intermediate tube member 76D and the outer tube member 42D. After that, in a state in which insertion of the main body section 40D into the vaginal canal 110 is terminated and the abutting section 49D contacts with the first portion 101, as shown in FIG. 47, the intermediate tube member 76D is moved toward the proximal side of the outer tube member 42D. As a result, the wire 78D of the anchor 77D is pushed toward the outside of the outer tube member 42D through the penetration hole 75D of the outer circumferential surface of the outer tube member 42D. The wire 78D of the anchor 77D is curved to be directed outward in the radial direction of the outer tube member 42D by the inner surface of the penetration hole 75D of the outer circumferential surface of the outer tube member 42D. For this reason, in the outside of the outer tube member 42D, in a state in which the wire 78D of the anchor 77D is inclined to be gradually separated from the outer circumferential surface of the outer tube member 42D toward the proximal side of the outer tube member 42D, the end section member 79D presses the vaginal wall 111.

As a result, the wire 78D of the anchor 77D presses the vaginal wall 111 outward in the radial direction via the end section member 79D. Like the locking section 43 described in the second embodiment, the outer tube member 42D is locked to the vaginal wall 111 by the frictional force between the end section members 79D fixed to the wires 78D of the anchors 77D and the vaginal wall 111.

After the outer tube member 42D is locked to the vaginal wall 111 by the locking section 43D having the anchors 77D, the second conductive member 8 protruding from the opening section 12 of the second insulating member 11 protrudes from the guide hole 52D. Accordingly, like the second embodiment, the distal end of the second conductive member 8 penetrates the vaginal wall 111, and the second conductive member 8 penetrates the vaginal wall 111 at the boundary portion between the uterine cervix 102 and the vaginal canal 110 (see FIG. 48).

Figure 49:
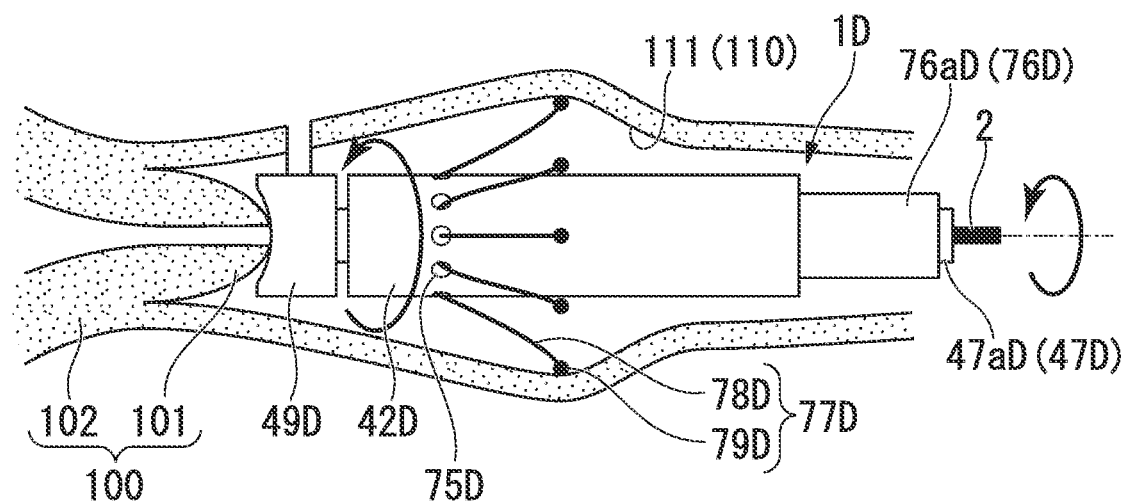
FIG. 49 is a view used to explain the procedure using the incision instrument according to the fifth embodiment of the present invention.

Next, the operator houses the second conductive member 8 in the second insulating member 11 like the first embodiment. Further, as shown in FIG. 49, the operator rotates the second gripping section 47aD about the centerline of the inner tube member 47D serving as a rotational center in a state in which the high frequency current is applied to the first conductive member 5. As a result, the first conductive member 5 rotates about the centerline of the vaginal canal 110 serving as a rotational center with respect to the vaginal wall 111 locked with respect to the outer tube member 42D by the locking section 43D. Accordingly, like the second embodiment, the first conductive member 5 dissects the vaginal wall 111 throughout the entire circumference.

Like the second embodiment, the incision instrument 1D according to the embodiment can also easily dissect the vaginal wall 111 along the ideal dissection line in the boundary between the uterine cervix 102 and the vaginal canal 110.

In the embodiment, manipulation of appropriately adjusting the length of the wire 78D of the anchor 77D can be easily performed by adjusting a rotational amount of the intermediate tube member 76D with respect to the outer tube member 42D.

Hereinabove, while the embodiments of the present invention have been described with reference to the accompanying drawings, specific configurations are not limited to the embodiments and may include design changes without departing from the spirit of the present invention.

For example, while the example in which the conductor through which the high frequency current is applied is exemplarily used in the incision section 4 had been described in the above-mentioned embodiments, the incision section 4 may have a heat probe.

Instead of the incision section including the conductor, an incision section configured to incise the biological tissue using ultrasonic waves or a laser may be installed at the incision instrument of the present invention. For example, when the incision section has a configuration using ultrasonic waves, a contact section switches a supply state of electric power to drive the ultrasonic vibrator in the incision section. In addition, when the incision section is configured to use the laser, the contact section switches the path of a laser beam.

Hereinabove, while the embodiments of the present invention have been described, the technical scope of the present invention is not limited to the above-mentioned embodiments, changes in combination of components in the embodiments, additions of various modifications to the components, or removal of the components may be made without departing from the spirit of the present invention. The present invention is not limited to the above-mentioned description but limited only the scope of the accompanying drawings.

What is claimed is:

1. An incision instrument comprising:
   an insertion section that is configured to be inserted into a body; and
   a manipulation section provided at a proximal end of the insertion section;
   wherein the insertion section comprises:
   a first insulating member which has an elongated tubular shape, and
   an incision section inserted within the first insulating member;
   wherein the incision section comprises:
   a first conductive member which has a tubular shape and has conductivity;
   a second conductive member disposed so as to movable inside the first conductive member along a longitudinal axis of the first conductive member, an outer diameter of the second conductive member being smaller than an inner diameter of the first conductive member;
   a contact section provided on an outer circumference surface of the second conductive member, formed to be larger than the outer diameter of the second conductive member, and including a conductor configured to contact an inner surface of the first conductive member; and a second insulating member which includes: a proximal end portion which has an outer circumference surface and an inner circumference surface, the outer circumference surface of the proximal end portion extends inside a distal end of the first conductive member and is fixed to the distal end of the first conductive member, the inner circumference surface of the proximal end portion forming a space where the contact section is configured to move; and a distal end portion in which an opening section is opened to communicate with the space and through which the second conductive member is capable of protruding and retracting via the opening section, the distal end portion being formed at a distal end surface of the distal end portion, and wherein the manipulation section comprises:

a manipulation main body section fixed to a proximal end of the first insulating member, and a handle member attached to the manipulation main body section to be movable with respect to the manipulation main body section and to advance and retract the second conductive member with respect to the first conductive member; and wherein the second insulating member is positioned between the contact section and the first conductive member in a state in which the second conductive member is protruded from the opening section of the second insulating member.

2. The incision instrument according to claim 1, wherein the second conductive member is reciprocally movable between a storage position at which a distal end of the second conductive member is disposed in the second insulating member and an exposure position at which the second conductive member is exposed outside the second insulating member.

3. The incision instrument according to claim 2, wherein the manipulation section has a connector configured to apply a high frequency current to the second conductive member, the contact section is configured to be separated from the first conductive member in a state in which the second conductive member is positioned at the exposure position and is configured to come in contact with the first conductive member in a state in which the second conductive member is positioned at the storage position such that the second conductive member and the first conductive member are in a conduction state, and the first conductive member is configured to be applied a high frequency current from the second conductive member via the contact section only when the contact section is in contact with the first conductive member.

4. The incision instrument according to claim 3, wherein the manipulation section has a stopper member configured to fix the second conductive member to the first conductive member in a state in which the contact section and the first conductive member are in contact with each other.

5. The incision instrument according to claim 1, wherein an exterior dimension of the second insulating member in a radial direction of the first conductive member is larger than an exterior dimension of the first conductive member in the radial direction of the first conductive member.

6. The incision instrument according to claim 1, wherein, along a longitudinal axis, a length of the contact section is shorter than a length of the second insulating member.

7. An incision instrument comprising:
an insertion section that is configured to be inserted into a body; and
a manipulation section provided at a proximal end of the insertion section;
wherein the insertion section comprises:
a first insulating member which has an elongated tubular shape, and
an incision section inserted within the first insulating member;
wherein the incision section comprises:
a first conductive member which has a tubular tapered section that has an inner surface that is inclined to form a conical shape such that an inner diameter of the inner surface at a distal side is larger than an inner diameter of the inner surface at a proximal side, the first conductive member having conductivity;
a second conductive member disposed so as to movable inside the first conductive member along a longitudinal axis of the first conductive member, an outer diameter of the second conductive member being smaller than an inner diameter of the first conductive member;
a contact section provided on an outer circumference surface of the second conductive member, formed to be larger than the outer diameter of the second conductive member, and a proximal end of the contact section has a conical-shaped conductor configured to contact an inner surface of the tapered section of the first conductive member; and
a second insulating member which includes: a proximal end portion which has an outer circumference surface and an inner circumference surface, the outer circumference surface of the proximal end portion extends inside a distal end of the first conductive member and is fixed to the distal end of the first conductive member, the inner circumference surface of the proximal end portion forming a space where the contact section is configured to move; and a distal end portion in which an opening section is opened to communicate with the space and through which the second conductive member is capable of protruding and retracting via the opening section, the distal end portion being formed at a distal end surface of the distal end portion, and
wherein the manipulation section comprises:
a manipulation main body section fixed to a proximal end of the first insulating member, and
a handle member attached to the manipulation main body section to be movable with respect to the manipulation main body section and to advance and retract the second conductive member with respect to the first conductive member; and
wherein the second insulating member is positioned between the contact section and the first conductive member in a state in which the second conductive member is protruded from the opening section of the second insulating member.

* * * * *